US011845772B2

(12) United States Patent
Issa et al.

(10) Patent No.: US 11,845,772 B2
(45) Date of Patent: *Dec. 19, 2023

(54) RIBONUCLEIC ACID PURIFICATION

(71) Applicant: ModernaTX, Inc., Cambridge, MA (US)

(72) Inventors: William Joseph Issa, Roslindale, MA (US); John Grant Aunins, Cambridge, MA (US); Stephane Bancel, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,187

(22) Filed: Jun. 30, 2022

(65) Prior Publication Data

US 2023/0203086 A1 Jun. 29, 2023

Related U.S. Application Data

(63) Continuation of application No. 14/776,864, filed as application No. PCT/US2014/026842 on Mar. 13, 2014, now Pat. No. 11,377,470.

(60) Provisional application No. 61/794,842, filed on Mar. 15, 2013.

(51) Int. Cl.

| | |
|---|---|
| *C07H 21/02* | (2006.01) |
| *C12Q 1/6806* | (2018.01) |
| *C12N 15/10* | (2006.01) |
| *C07H 1/06* | (2006.01) |
| *C08B 37/00* | (2006.01) |

(52) U.S. Cl.
CPC ............ *C07H 21/02* (2013.01); *C07H 1/06* (2013.01); *C08B 37/0039* (2013.01); *C12N 15/1006* (2013.01); *C12Q 1/6806* (2013.01)

(58) Field of Classification Search
CPC ........ C12Q 1/6806; C07H 1/06; C07H 21/02; C08Q 37/0039; C12N 15/1006
USPC .................................. 536/18.1, 18.5, 25.41
See application file for complete search history.

(56) References Cited

U.S. PATENT DOCUMENTS

| | | | |
|---|---|---|---|
| 4,870,015 A | 9/1989 | Hoffman | |
| 5,426,180 A | 6/1995 | Kool | |
| 5,489,677 A | 2/1996 | Sanghvi et al. | |
| 5,512,439 A * | 4/1996 | Hornes | G01N 33/54326 |
| | | | 436/526 |
| 5,591,722 A | 1/1997 | Montgomery et al. | |
| 5,637,459 A | 6/1997 | Burke et al. | |
| 5,639,873 A | 6/1997 | Barascut et al. | |
| 5,641,400 A | 6/1997 | Kaltenbach et al. | |
| 5,789,578 A | 8/1998 | Burton et al. | |
| 5,808,039 A | 9/1998 | Reddy et al. | |
| 5,989,911 A | 11/1999 | Fournier et al. | |
| 6,011,148 A | 1/2000 | Bussey et al. | |
| 6,022,715 A | 2/2000 | Merenkova et al. | |
| 6,022,737 A | 2/2000 | Niven et al. | |
| 6,217,899 B1 | 4/2001 | Benameur et al. | |
| 6,248,268 B1 | 6/2001 | Cook | |
| 6,303,378 B1 | 10/2001 | Bridenbaugh et al. | |
| 6,391,542 B1 | 5/2002 | Anderson et al. | |
| 6,423,492 B1 | 7/2002 | Harbron | |
| 6,511,832 B1 | 1/2003 | Guarino et al. | |
| 6,521,411 B2 | 2/2003 | Hecker et al. | |
| 6,642,374 B2 | 11/2003 | Gjerde et al. | |
| 6,812,341 B1 * | 11/2004 | Conrad | C12N 15/10 |
| | | | 536/25.4 |
| 6,881,314 B1 | 4/2005 | Wang et al. | |
| 7,691,569 B2 | 4/2010 | Wohlgemuth et al. | |
| 7,745,391 B2 | 6/2010 | Mintz et al. | |
| 7,939,031 B2 | 5/2011 | Angus et al. | |
| 8,075,780 B2 | 12/2011 | Pearce | |
| 8,093,367 B2 | 1/2012 | Kore et al. | |
| 8,664,194 B2 | 3/2014 | de Fougerolles et al. | |
| 8,680,069 B2 | 3/2014 | de Fougerolles et al. | |
| 8,691,750 B2 | 4/2014 | Constien et al. | |
| 8,710,200 B2 | 4/2014 | Schrum et al. | |
| 8,716,465 B2 | 5/2014 | Rossi et al. | |
| 8,802,438 B2 | 8/2014 | Rossi et al. | |
| 8,822,663 B2 | 9/2014 | Schrum et al. | |
| 8,883,506 B2 | 11/2014 | Rossi et al. | |
| 8,898,864 B1 | 12/2014 | Porter | |
| 8,969,353 B2 | 3/2015 | Mahon et al. | |
| 8,980,864 B2 | 3/2015 | Hoge et al. | |

(Continued)

FOREIGN PATENT DOCUMENTS

| | | |
|---|---|---|
| CA | 2028849 A1 | 9/1991 |
| CA | 2473135 A1 | 6/2003 |

(Continued)

OTHER PUBLICATIONS

Bryant, The Nucleic Acids Protocols Handbook, Rapley (Ed), 2000, pp. 9-11.*
Kuwahara et al., "Molecular evolution of functional nucleic acids with chemical modifications," Molecules. 15(8):5423-44 (2010).
Li et al., "Effects of chemically modified messenger RNA on protein expression," Bioconjug Chem. 27(3):849-53 (2016).
Yanagawa et al., "Overexpression of autocrine motility factor in metastatic tumor cells: possible association with augmented expression of KIF3A and GDI-beta," Lab Invest. 84(4):513-22 (2004).
Takita et al., "Precise sequential DNA ligation on a solid substrate: solid-based rapid sequential ligation of multiple DNA molecules," DNA Res. 20(6):583-92 (Dec. 2013).
RNA Modification Database Entry for 1-methylpseudouridine <https://mods.rna.albany.edu/mods/modifications/view/55>, retrieved on Feb. 26, 2019 (1 page).

(Continued)

*Primary Examiner* — Ganapathy Krishnan
(74) *Attorney, Agent, or Firm* — Clark & Elbing LLP

(57) ABSTRACT

Disclosed herein are methods for purifying RNA comprising poly A. Also disclosed herein are compositions such as surfaces and oligonucleotides for purifying RNA comprising polyA. Other embodiments are also disclosed. Commercially-available resins having polythymidine oligonucleotide ligands typically contain less than 30 thymidine (2'deoxy) residues and some commercial resin suppliers utilize a distribution of dT chain lengths, not of a discreet length.

16 Claims, 17 Drawing Sheets

(56) References Cited

U.S. PATENT DOCUMENTS

| | | |
|---|---|---|
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,751,925 B2 | 9/2017 | Hoge et al. |
| 9,803,177 B2 | 10/2017 | Rossi et al. |
| 9,872,900 B2 | 1/2018 | Ciaramella et al. |
| 9,950,068 B2 | 4/2018 | De Fougerolles et al. |
| 10,022,435 B2 | 7/2018 | Ciaramella et al. |
| 10,064,935 B2 | 9/2018 | Ciaramella et al. |
| 10,072,057 B2 | 9/2018 | Hoge et al. |
| 10,286,086 B2 | 5/2019 | Roy et al. |
| 10,898,574 B2 | 1/2021 | de Fougerolles et al. |
| 11,377,470 B2 * | 7/2022 | Issa .................... C07H 1/06 |
| 2001/0025097 A1 | 9/2001 | Sheridan et al. |
| 2002/0001812 A1 | 1/2002 | Smith et al. |
| 2002/0016450 A1 | 2/2002 | Laugharn et al. |
| 2002/0058256 A1 | 5/2002 | Rothberg et al. |
| 2002/0062017 A1 | 5/2002 | Hecker et al. |
| 2002/0114784 A1 | 8/2002 | Li et al. |
| 2002/0130430 A1 | 9/2002 | Castor |
| 2002/0153312 A1 | 10/2002 | Gjerde et al. |
| 2003/0120035 A1 | 6/2003 | Gao et al. |
| 2003/0170810 A1 | 9/2003 | Vedadi et al. |
| 2003/0170876 A1 | 9/2003 | Widner et al. |
| 2003/0170891 A1 | 9/2003 | McSwiggen |
| 2003/0180754 A1 | 9/2003 | Bergholtz et al. |
| 2003/0180779 A1 | 9/2003 | Lofton-Day et al. |
| 2003/0207288 A1 | 11/2003 | Lewin et al. |
| 2004/0038278 A1 | 2/2004 | Tzertzinis et al. |
| 2004/0076978 A1 | 4/2004 | Verfaillie |
| 2004/0142433 A1 | 7/2004 | Padgett et al. |
| 2004/0220127 A1 | 11/2004 | Sternberg et al. |
| 2004/0224425 A1 | 11/2004 | Gjerde et al. |
| 2004/0259097 A1 | 12/2004 | De Backer et al. |
| 2004/0259240 A1 | 12/2004 | Fadden |
| 2005/0003496 A1 | 1/2005 | McGall et al. |
| 2005/0053942 A1 | 3/2005 | Kauppinen et al. |
| 2005/0130196 A1 | 6/2005 | Hofstadler et al. |
| 2005/0171333 A1 | 8/2005 | Paulsen |
| 2006/0003371 A1 | 1/2006 | Russell et al. |
| 2006/0057566 A1 | 3/2006 | Van Ness et al. |
| 2006/0058266 A1 | 3/2006 | Manoharan et al. |
| 2006/0121441 A1 | 6/2006 | Spira |
| 2006/0223081 A1 | 10/2006 | Jarrell et al. |
| 2006/0257935 A1 | 11/2006 | Takeshita et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0076910 A1 | 3/2008 | Takkellapati et al. |
| 2008/0139801 A1 | 6/2008 | Umansky et al. |
| 2008/0153078 A1 | 6/2008 | Braman et al. |
| 2008/0171711 A1 | 7/2008 | Hoerr et al. |
| 2008/0274463 A1 | 11/2008 | Chen et al. |
| 2008/0311140 A1 | 12/2008 | Lee et al. |
| 2009/0099041 A1 | 4/2009 | Church et al. |
| 2009/0192303 A1 | 7/2009 | Skagestad |
| 2009/0215125 A1 | 8/2009 | Reed et al. |
| 2009/0264511 A1 | 10/2009 | de Fougerolles et al. |
| 2009/0270278 A1 | 10/2009 | Lim et al. |
| 2009/0286852 A1 | 11/2009 | Kariko et al. |
| 2009/0286955 A1 | 11/2009 | Hatala et al. |
| 2010/0015232 A1 | 1/2010 | Besenbacher et al. |
| 2010/0047261 A1 | 2/2010 | Hoerr et al. |
| 2010/0048883 A1 | 2/2010 | Ketterer et al. |
| 2010/0159456 A1 | 6/2010 | Albitar |
| 2010/0178272 A1 | 7/2010 | Hartmann et al. |
| 2010/0183639 A1 | 7/2010 | Uhlmann et al. |
| 2010/0255574 A1 | 10/2010 | Rosen et al. |
| 2010/0261228 A1 | 10/2010 | Gharib et al. |
| 2010/0261231 A1 | 10/2010 | Kore et al. |
| 2010/0317532 A1 | 12/2010 | Liu et al. |
| 2011/0130440 A1 | 6/2011 | Manoharan et al. |
| 2011/0143397 A1 | 6/2011 | Kariko et al. |
| 2011/0218170 A1 | 9/2011 | Thottassery et al. |
| 2011/0244026 A1 | 10/2011 | Guild et al. |
| 2011/0281938 A1 | 11/2011 | Schaub et al. |
| 2011/0294205 A1 | 12/2011 | Hukari et al. |
| 2012/0009222 A1 | 1/2012 | Nguyen et al. |
| 2012/0021042 A1 | 1/2012 | Panzner et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0251618 A1 | 10/2012 | Schrum et al. |
| 2012/0309053 A1 | 12/2012 | Wellings |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | de Fougerolles et al. |
| 2013/0115274 A1 | 5/2013 | Knopov et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245105 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0241956 A1 | 8/2014 | Page et al. |
| 2014/0243399 A1 | 8/2014 | Schrum et al. |
| 2014/0275227 A1 | 9/2014 | Hoge et al. |
| 2014/0343129 A1 | 11/2014 | de Fougerolles et al. |
| 2014/0371302 A1 | 12/2014 | Afeyan et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0044758 A1 | 2/2015 | Amshey et al. |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0105275 A1 | 4/2015 | Wong et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0157781 A1 | 6/2015 | Kyle et al. |
| 2015/0166616 A1 | 6/2015 | Bancel et al. |
| 2015/0167017 A1 | 6/2015 | Roy et al. |
| 2015/0174070 A1 | 6/2015 | Cheng et al. |
| 2015/0211039 A1 | 7/2015 | Wang et al. |
| 2015/0291678 A1 | 10/2015 | Rudolph et al. |
| 2015/0307542 A1 | 10/2015 | Roy et al. |
| 2016/0017313 A1 | 1/2016 | Spivak et al. |
| 2016/0024139 A1 | 1/2016 | Berlanda Scorza et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0025630 A1 | 1/2016 | Jensen et al. |
| 2016/0032273 A1 | 2/2016 | Shahrokh et al. |

(56) References Cited

U.S. PATENT DOCUMENTS

| | | |
|---|---|---|
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367702 A1 | 12/2016 | Hoge et al. |
| 2017/0088888 A1 | 3/2017 | El-Sagheer et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| CN | 105087552 A | 11/2015 |
| DE | 10 2006 051 516 A1 | 5/2008 |
| EP | 0366400 A2 | 5/1990 |
| EP | 1083232 B1 | 2/2005 |
| EP | 1611899 A1 | 1/2006 |
| EP | 1619254 A1 | 1/2006 |
| EP | 1383556 B9 | 3/2008 |
| EP | 1831160 B1 | 6/2010 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2011-130725 A | 7/2011 |
| RU | 2540017 C2 | 1/2015 |
| WO | WO-91/05058 A1 | 4/1991 |
| WO | WO-93/03052 A1 | 2/1993 |
| WO | WO-93/13121 A1 | 7/1993 |
| WO | WO-98/05673 A1 | 2/1998 |
| WO | WO-01/55306 A2 | 8/2001 |
| WO | WO-01/81566 A2 | 11/2001 |
| WO | WO-02/44399 A2 | 6/2002 |
| WO | WO-2002/098443 A2 | 12/2002 |
| WO | WO-03/039523 A2 | 5/2003 |
| WO | WO-03/051881 A1 | 6/2003 |
| WO | WO-2004/020575 A2 | 3/2004 |
| WO | WO-2004/020576 A2 | 3/2004 |
| WO | WO-2004/064782 A2 | 8/2004 |
| WO | WO-2006/015445 A1 | 2/2006 |
| WO | WO-2007/024708 A2 | 3/2007 |
| WO | WO-2007/024798 A2 | 3/2007 |
| WO | WO-2007/089607 A2 | 8/2007 |
| WO | WO-2007/120863 A2 | 10/2007 |
| WO | WO-2008/039669 A1 | 4/2008 |
| WO | WO-2008/045505 A2 | 4/2008 |
| WO | WO-2008/083949 A2 | 7/2008 |
| WO | WO-2008/120016 A1 | 10/2008 |
| WO | WO-2009/016431 A1 | 2/2009 |
| WO | WO-2009/042971 A2 | 4/2009 |
| WO | WO-2009/051451 A2 | 4/2009 |
| WO | WO-2009/127060 A1 | 10/2009 |
| WO | WO-2009/127230 A1 | 10/2009 |
| WO | WO-2009/147519 A1 | 12/2009 |
| WO | WO-2009/149253 A2 | 12/2009 |
| WO | WO-2010/014895 A2 | 2/2010 |
| WO | WO-2010/017510 A1 | 2/2010 |
| WO | WO-2010/054401 A1 | 5/2010 |
| WO | WO-2010/109289 A1 | 9/2010 |
| WO | WO-2010/144740 A1 | 12/2010 |
| WO | WO-2011/005850 A1 | 1/2011 |
| WO | WO-2011/012316 A3 | 2/2011 |
| WO | WO-2011/068810 A1 | 6/2011 |
| WO | WO-2011/071931 A2 | 6/2011 |
| WO | WO-2011/127933 A1 | 10/2011 |
| WO | WO-2011/130624 A2 | 10/2011 |
| WO | WO-2011/133868 A2 | 10/2011 |
| WO | WO-2011/140627 A1 | 11/2011 |
| WO | WO-2012/019168 A2 | 2/2012 |
| WO | WO-2012/077080 A1 | 6/2012 |
| WO | WO-2012/135805 A2 | 10/2012 |
| WO | WO-2012/138530 A1 | 10/2012 |
| WO | WO-2012/158736 A1 | 11/2012 |
| WO | WO-2012/164565 A1 | 12/2012 |
| WO | WO-2013/036748 A1 | 3/2013 |
| WO | WO-2013/039857 A1 | 3/2013 |
| WO | WO-2013/039861 A2 | 3/2013 |
| WO | WO-2013/052523 A1 | 4/2013 |
| WO | WO-2013/064911 A2 | 5/2013 |
| WO | WO-2013/090186 A1 | 6/2013 |
| WO | WO-2013/090294 A1 | 6/2013 |
| WO | WO-2013/090648 A1 | 6/2013 |
| WO | WO-2013/090897 A1 | 6/2013 |
| WO | WO-2013/096709 A2 | 6/2013 |
| WO | WO-2013/101690 A1 | 7/2013 |
| WO | WO-2013/103659 A1 | 7/2013 |
| WO | WO-2013/113326 A1 | 8/2013 |
| WO | WO-2013/113501 A1 | 8/2013 |
| WO | WO-2013/113502 A1 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151669 A1 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/184976 A2 | 12/2013 |
| WO | WO-2013/185069 A1 | 12/2013 |
| WO | WO-2014/028429 A2 | 2/2014 |
| WO | WO-2014/081507 A1 | 5/2014 |
| WO | WO-2014/093574 A1 | 6/2014 |
| WO | WO-2014/093622 A2 | 6/2014 |
| WO | WO-2014/093924 A1 | 6/2014 |
| WO | WO-2014/113089 A2 | 7/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/160243 A1 | 10/2014 |
| WO | WO-2014/160284 A1 | 10/2014 |
| WO | WO-2014/164253 A1 | 10/2014 |
| WO | WO-2015/006747 A2 | 1/2015 |
| WO | WO-2015/023975 A1 | 2/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/051214 A1 | 4/2015 |
| WO | WO-2015/058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101414 A2 | 7/2015 |
| WO | WO-2015/101416 A1 | 7/2015 |
| WO | WO-2015/105926 A1 | 7/2015 |
| WO | WO-2015/179598 A2 | 11/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/010840 A1 | 1/2016 |
| WO | WO-2016/011222 A2 | 1/2016 |
| WO | WO-2016/011226 A1 | 1/2016 |
| WO | WO-2016/034620 A1 | 3/2016 |

(56) References Cited

FOREIGN PATENT DOCUMENTS

| | | |
|---|---|---|
| WO | WO-2016/036902 A1 | 3/2016 |
| WO | WO-2016/077125 A1 | 5/2016 |
| WO | WO-2016/118724 A1 | 7/2016 |
| WO | WO-2016/118725 A1 | 7/2016 |

OTHER PUBLICATIONS

Applied Biosystems, DNA Synthesizer Model 380B, Version 1.1 User's Manual, 2001 (327 pages).
Aviv et al., "Purification of Biologically Active Globin Messenger RNA by Chromatography on Oligothymidylic acid-Cellulose," Proc Nat Acad Sci USA 69(6):1408-1412 (1972).
Bell et al., "In trans T cell tolerance diminishes autoantibody responses and exacerbates experimental allergic encephalomyelitis," J Immunol. 180(3):1508-16 (2008).
Rodriguez et al., "Magnetic poly (styrene/divinylbenzene/acrylic acid)-based hybrid microspheres for bio-molecular recognition," Micro Nano Lett. 6(6):349-352 (2011).
Brand et al., "Biosynthesis of a Hypermodified Nucleotide in *Saccharomyces carlsbergensis* 17S and HeLa-Cell 18S Ribosomal Ribonucleic Acid," Biochem J. 169(1):71-77 (1978) (9 pages).
Bryant et al., Chapter 2: Isolation of mRNA by Affinity Chromatography. *The Nucleic Acid Protocols Handbook.* Springer, 9-11 (2000) (4 pages).
Tavernier et al., "mRNA as gene therapeutic: how to control protein expression," J Control Release. 150(3):238-47 (2011).
Salfen et al., "Effects of exogenous ghrelin on feed intake, weight gain, behavior, and endocrine responses in weanling pigs," J Anim Sci. 82(7):1957-66 (2004).
Chen et al., "LC/MS analysis of cellular RNA reveals NAD-linked RNA," Nat Chem Biol. 5(12):879-81 (2009).
Deltcheva et al., "CRISPR RNA maturation by trans-encoded small RNA and host factor RNase III," available in PMC Sep. 30, 2011, published in final edited form as: Nature. 471(7340):602-7 (2011) (54 pages).
Dickman, "Ion Pair Reverse-Phase Chromatography: A Versatile Platform for the Analysis of RNA," <http://www.chromatographytoday.com/articles/prep-chiral-green-incsfc-gpc-ion/33/m._j._dickman/ion_pair_reverse-phase_chromatography_a_versatile_platform_for_the_analysis_of_rna/984/>, retrieved on Oct. 16, 2015 (5 pages).
Santner et al., "Efficient access to 3'-terminal azide-modified RNA for inverse click-labeling patterns," Bioconjug Chem. 25(1):188-95 (Jan. 2014).
El-Sagheer et al., "Click nucleic acid ligation: applications in biology and nanotechnology," Acc Chem Res. 45(8):1258-67 (2012).
Extended European Search Report for European Application No. 14770466.2, dated Sep. 28, 2016 (10 pages).
Thess et al., "Sequence-engineered mRNA without chemical nucleoside modifications enables an effective protein therapy in large animals," Mol Ther. 23(9):1456-64 (2015).
Sasaki et al., "Construction of a normalized cDNA library by introduction of a semi-solid mRNA-cDNA hybridization system," Nucleic Acids Res. 22(6):987-92 (1994).
Finn et al., "A Single Administration of CRISPR/Cas9 Lipid Nanoparticles Achieves Robust and Persistent In Vivo Genome Editing," Cell Rep. 22(9):2227-2235 (2018) (17 pages).
Gaj et al., "ZFN, TALEN, and CRISPR/Cas-based methods for genome engineering," Trends Biotechnol. 31(7):397-405 (Jul. 2013).
Gilham, "The Synthesis of Polynucleotide-Celluloses and Their Use in the Fractionation of Polynucleotides," J Am Chem Soc. 86(22):4982-4985 (1964).
Shimelis et al., "Nuclease P1 digestion/high-performance liquid chromatography, a practical method for DNA quantitation," J Chromatogr A. 1117(2):132-6 (2006).
Goodnow, "Pathways for self-tolerance and the treatment of autoimmune diseases," Lancet. 357(9274):2115-21 (2001).
Grosjean, Modification and editing of RNA: historical overview and important facts to remember. *Fine-Tuning of RNA Functions by Modification and Editing.* Grosjean H, 1-22 (2005).
Thess et al., Supplementary material for "Sequence-engineered mRNA without chemical nucleoside modifications enables an effective protein therapy in large animals," Mol Ther. 23(9):1456-64 (2015), accessed via <https://www.sciencedirect.com/science/article/pii/S1525001616302738#cesec90> (11 Pages).
Skyler et al., "Effects of oral insulin in relatives of patients with type 1 diabetes: The Diabetes Prevention Trial—Type 1," Diabetes Care 28(5):1068-76 (2005).
Hansen et al., "Circular RNA and miR-7 in Cancer," Cancer Res. 73(18):5609-12 (Sep. 2013).
Hansen et al., "Natural RNA circles function as efficient microRNA sponges," Nature. 495(7441):384-8 (Feb. 2013) (7 pages).
Henke et al., "microRNA-122 stimulates translation of hepatitis C virus RNA," EMBO J. 27(24):3300-10 (2008).
Slater, Chapter 16: The Purification of Poly(A)-Containing RNA by Affinity Chromatography. Methods in Molecular Biology. ed. Walker, Springer Verlag, 117-20 (1985).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
International Preliminary Report on Patentability and Written Opinion for International Patent Application No. PCT/US2014/026842, dated Sep. 15, 2015 (6 pages).
Virnekäs et al., "Trinucleotide phosphoramidites: ideal reagents for the synthesis of mixed oligonucleotides for random mutagenesis," Nucleic Acids Res. 22(25):5600-7 (1994).
Smith et al., "Purification of polynucleotide phosphorylase by affinity chromatography and some properties of the purified enzymes," Nucleic Acids Res. 1(12):1763-73 (1974).
Jani et al., "In vitro transcription and capping of Gaussia luciferase mRNA followed by HeLa cell transfection," J Vis Exp. 61:e3702 (2012) (9 pages).
Jawalekar et al., "Oligonucleotide tagging for copper-free click conjugation," Molecules. 18(7):7346-63 (Jul. 2013).
Karikó et al., "Incorporation of pseudouridine into mRNA yields superior nonimmunogenic vector with increased translational capacity and biological stability." Mol Ther. 16(11):1833-40 (2008).
Sonoke et al., "Tumor regression in mice by delivery of Bcl-2 small interfering RNA with pegylated cationic liposomes," Cancer Res. 68(21):8843-51 (2008) (10 pages).
Karikó et al., "mRNA is an endogenous ligand for Toll-like receptor 3," J Biol Chem. 279(13):12542-50 (2004).
Karikó et al., "Naturally occurring nucleoside modifications suppress the immunostimulatory activity of RNA: Implication for therapeutic RNA development," Curr Opin Drug Discov Devel. 10(5): 523-532 (2007).
Vomelová et al., "Methods of RNA purification. All ways (should) lead to Rome," Folia Biol (Praha). 55(6):243-51 (2009).
St. Claire, "Positive ion electrospray ionization tandem mass spectrometry coupled to ion-pairing high-performance liquid chromatography with a phosphate buffer for the quantitative analysis of intracellular nucleotides," Rapid Commun Mass Spectrom. 14(17):1625-34 (2000).
"AutoImmune shares collapse on Colloral data in rheumatoid arthritis," Pharma MarketLetter, *Marketletter Publications Ltd.* ISSN:0951-3175 (1999) (2 pages).
Kore et al., "Synthesis and application of 2'-fluoro-substituted cap analogs," Bioorg Med Chem Letters. 17:5295-9 (2007).
Kraus et al., "Oral tolerance and inflammatory bowel disease," Curr Opin Gastroenterol. 21(6):692-6 (2005).
Stocher et al., "Removal of Template DNA From cRNA Preparations by Combined Oligo (dT) Affinity Chromatography and DNase I Digestion," Biotechniques. 36(3):480-2 (2004).
Kuribayashi-Ohta et al., "Application of oligo(dT)30-latex for rapid purification of poly(A)+ mRNA and for hybrid subtraction with the in situ reverse transcribed cDNA," Biochim Biophys Acta. 1156(2):204-12 (1993).
Quabius et al., "Synthetic mRNAs for manipulating cellular phenotypes: an overview," N Biotechnol. 32(1):229-35 (2015).

(56) References Cited

OTHER PUBLICATIONS

Wang et al., "One-step generation of mice carrying mutations in multiple genes by CRISPR/Cas-mediated genome engineering," Cell. 153(4):910-8 (May 2013).
Liu et al., "Construction of circular miRNA sponges targeting miR-21 or miR-221 and demonstration of their excellent anticancer effects on malignant melanoma cells," Int J Biochem Cell Biol. 45(11):2643-50 (Nov. 2013).
Azarani et al., "RNA analysis by ion-pair reversed-phase high performance liquid chromatography," Nucleic Acids Res. 29(2):E7 (2001) (9 pages).
Lukavsky et al., "Large-scale Preparation and Purification of Polyacrylamide-Free RNA Oligonucleotides," RNA. 10(5):889-93 (2004) (6 pages).
Bélanger et al., "Characterization of hMTr1, a human Cap1 2'-O-ribose methyltransferase," J Biol Chem. 285(43):33037-44 (2010).
McKenna et al. "Purification and characterization of transcribed RNAs using gel filtration chromatography." Nat Protoc. 2(12):3270-7 (2007).
Derrigo et al., "RNA-protein interactions in the control of stability and localization of messenger RNA (review)," Int J Mol Med. 5(2):111-23 (2000).
Memczak et al., "Circular RNAs are a large class of animal RNAs with regulatory potency," Nature. 495(7441):333-8 (Feb. 2013) (10 pages).
Warren et al., "Highly efficient reprogramming to pluripotency and directed differentiation of human cells with synthetic modified mRNA," Cell Stem Cell. 7(5):618-30 (2010).
Moretti et al., "Mechanism of translational regulation by miR-2 from sites in the 5' untranslated region or the open reading frame," RNA. 16(12):2493-502 (2010).
Gilbert et al., "CRISPR-mediated modular RNA-guided regulation of transcription in eukaryotes," Cell. 154(2):442-51 (Jul. 2013) (15 pages).
Myllykoski et al., "Expression, Purification, and Initial Characterization of Different Domains of Recombinant Mouse 2',3'-cyclic Nucleotide 3'-phosphodiesterase, an Enigmatic Enzyme From the Myelin Sheath," BMC Res Notes. 3:12 (2010) (7 pages).
Hamaguchi et al., "Direct reverse transcription-PCR on oligo(dT)-immobilized polypropylene microplates after capturing total mRNA from crude cell lysates," Clin Chem. 44(11):2256-63 (1998).
Nakazato et al., "Purification of messenger RNA and heterogeneous nuclear RNA containing poly(A) sequences," Methods Enzymol. 29:431-43 (1974).
Haseltine et al., "Rous sarcoma virus genome is terminally redundant: the 5' sequence," Proc Natl Acad Sci USA. 74(3):989-93 (1977).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Weiner et al., "Oral tolerance," available in PMC May 1, 2012, published in final edited form as: Immunol Rev. 241(1):241-59 (2011) (14 pages).
Pascolo, Chapter 3: Vaccination With Messenger RNA. *Methods in Molecular Medicine, vol. 127: DNA Vaccines: Methods and Protocols: Second Edition.* Saltzman et al., Humana Press Inc., 23-40 (2006).
Kanwar et al., "Chimeric aptamers in cancer cell-targeted drug delivery," Crit Rev Biochem Mol Bio. 46(6):459-77 (2011).
Pozzilli et al., "No effect of oral insulin on residual beta-cell function in recent-onset type I diabetes (the IMDIAB VII)," Diabetologia. 43(8):1000-4 (2000).
Kluiver et al., "Rapid generation of MicroRNA Sponges for MicroRNA Inhibition ," PLoS One. 7(1):E29275(2012) (8 pages).
PubChem Compound Summary for CID 479886, created Aug. 1, 2005. <URL: http://pubchem.ncbi.nlm.nih.gov/compound/479886> (12 pages).

Kormann et al., "Expression of therapeutic proteins after delivery of chemically modified mRNA in mice," Nat Biotechnol. 29(2):154-7 (including supplement) (2011) (6 pages).
Qiu et al., "Creating a flexible multiple microRNA expression vector by linking precursor microRNAs," Biochem Biophys Res Commun. 411(2):276-80 (2011).
Weiss et al., "Prophylactic mRNA vaccination against allergy," Curr Opin Allergy Clin Immunol. 10(6):567-74 (2010) (8 pages).
Loomis et al., "Strategies for modulating innate immune activation and protein production of in vitro transcribed mRNAs," J Mater Chem B. 4(9):1619-32 (2016).
Bynum et al., "Characterization of subcellular poly(A) RNA populations by poly(U) sepharose chromatography and discontinuous elution," Anal. Biochem. 107(2):406-16 (1980).
Melton et al., "Efficient in vitro synthesis of biologically active RNA and RNA hybridization probes from plasmids containing a bacteriophage SP6 promoter," Nucleic Acids Res. 12(18):7035-56 (1984).
Farrow et al., "Combinatorial recombination of gene fragments to construct a library of chimeras," Curr Protoc Protein Sci. Chapter 26, Unit 26.2 (2010) (20 pages).
Motorin, "RNA modification," eLS. John Wiley & Sons, DOI:10.1002/9780470015902.a0000528.pub3 (2015) (18 pages).
Gustafsson et al., "Codon bias and heterologous protein expression," Trends Biotechnol. 22(7):346-353 (2004).
Nielsen et al., "An mRNA is capped by a 2',5' lariat catalyzed by a group I-like ribozyme," Science. 309(5740):1584-7 (2005).
Weissman et al., "mRNA: Fulfilling the promise of gene therapy," Mol Ther. 23(9):1416-7 (2015).
Perez-Pinera et al., "RNA-guided gene activation by CRISPR-Cas9-based transcription factors," Nat Methods. 10(10):973-6 (Oct. 2013).
Kim et al. "Rapid purification of RNAs using fast performance liquid chromatography (FPLC)." RNA. 13(2):289-94 (2007).
Pyhtila et al., "Signal sequence- and translation-independent mRNA localization to the endoplasmic reticulum," RNA. 14(3):445-53 (2008).
Anderson, Bart R., Dissertation: "Nucleoside Modifications Suppress RNA Activation of Cytoplasmic RNA Sensors," Doctor of Philosophy, Cell & Molecular Biology, University of Pennsylvania, 2010 (197 pages).
Maeder et al., "CRISPR RNA-guided activation of endogenous human genes," Nat Methods 10(10):977-9 (Oct. 2013).
Extended European Search Report for European Application No. 18208038.2, dated Aug. 28, 2019 (7 pages).
Mészáros et al., "Subtractive hybridization strategy using paramagnetic oligo(dT) beads and PCR," Biotechniques. 20(3):413-9 (1996).
Wilusz et al., "Molecular Biology. A circuitous route to noncoding RNA," Science. 340(6131):440-1 (Apr. 2013).
PubChem Compound Summary for CID 262692, created Mar. 26, 2005. <URL: http://pubchem.ncbi.nlm.nih.gov/compound/262692> (11 pages).
Anderson et al., "Incorporation of pseudouridine into mRNA enhances translation by diminishing PKR activation," Nucleic Acids Res. 38(17):5884-92 (2010).
Mestas et al., "Of mice and not men: differences between mouse and human immunology," J Immunol. 172(5):2731-8 (2004).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Lietard et al., "New strategies for cyclization and bicyclization of oligonucleotides by click chemistry assisted by microwaves," J Org Chem. 73(1):191-200 (2008).
International Search Report for International Patent Application No. PCT/US2014/026835, dated Aug. 28, 2014 (4 pages).
Park et al., "Reverse transcriptase-coupled quantitative real time PCR analysis of cell-free transcription on the chromatin-assembled p21 promoter," PLoS One. 6(8):e23617 (2011) (6 pages).
Yamamoto et al., "Current prospects for mRNA gene delivery," Eur J Pharm Biopharm. 71(3):484-9 (2009).
Hornes et al., "Magnetic DNA hybridization properties of oligonucleotide probes attached to superparamagnetic beads and their use

(56) References Cited

OTHER PUBLICATIONS in the isolation of poly(A) mRNA from eukaryotic cells," Genet Anal Tech Appl. 7(6):145-50 (1990).
International Preliminary Report on Patentability for International Patent Application No. PCT/US2017/038426, dated Jan. 3, 2019 (8 pages).
Jakobsen et al., "Purification of mRNA directly from crude plant tissues in 15 minutes using magnetic oligo dT microspheres," Nucleic Acids Res. 18(12):3669 (1990).
Probst et al., "Spontaneous cellular uptake of exogenous messenger RNA in vivo is nucleic acid-specific, saturable and ion dependent," Gene Ther. 14(15):1175-1180 (2007).
International Search Report and Written Opinion for International Application No. PCT/US17/38426, dated Sep. 6, 2017 (15 pages).
Berensmeier, "Magnetic particles for the separation and purification of nucleic acids," Appl Microbiol Biotechnol. 73:495-504 (2006).
International Search Report and Written Opinion for International Application No. PCT/US2017/038534, dated Sep. 7, 2017 (15 pages).
Karikó et al., "Suppression of RNA recognition by Toll-like receptors: the impact of nucleoside modification and the evolutionary origin of RNA," Immunity. 23(2):165-75 (2005).
Technical Data Sheet for "BioMag® SelectaPure mRNA Purification System," Polysciences, Inc., dated Mar. 25, 2011 (5 page).
Data Sheet for "Dynabeads® mRNA Purification Kit" received Jan. 12, 2009 (2 pages).
International Preliminary Report on Patentability for International Patent Application No. PCT/US2017/038498, dated Jan. 3, 2019 (8 pages).
International Search Report and Written Opinion for International Application No. PCT/US2017/038498, dated Sep. 7, 2017 (15 pages).
Safarik et al., "Large-scale separation of magnetic bioaffinity adsorbents," Biotechnol. Lett. 23:1953-6 (2001).
Sahin et al., "mRNA-based therapeutics—developing a new class of drugs," Nat Rev Drug Discov. 13(10):759-80 (Sep. 2014).
"Resins for Solid Phase Peptide Synthesis—Core Resins," aappTec, <https://www.peptide.com/resources/resins-for-solid-phase-peptide-synthesis-core-resins/>, retrieved on Feb. 28, 2023 (5 Pages).
Dong et al., "Solid lipid nanoparticles: continuous and potential large-scale nanoprecipitation production in static mixers," Colloids Surf B Biointerfaces. 94:68-72 (2012).

\* cited by examiner

| Sample | Target | Sample | Chemistry | Description | Purification Method | Sample Conc. (ng/ul) | Endotoxin Level (Eu/mL) | Endotoxin Level (EU/mg) | Comment |
|---|---|---|---|---|---|---|---|---|---|
| 1 | GCSF | 12-04-90-C-A | Gen 1 | OligodT/UF Purified | GE Oligo dT illustra mRNA kit | 291 | >5 | >17 | Highly Contaminated |
| 2 | GCSF | 12-04-90-C-B | Gen 1 | OligodT/OligodT Purified | GE Oligo dT illustra mRNA kit | 350 | 3.99 | 11.4 | Highly Contaminated |
| 3 | GCSF | 12-04-91-C-A | Gen 2 | OligodT/UF Purified | GE Oligo dT illustra mRNA kit | 287 | >10 | 35 | Highly Contaminated |
| 4 | GCSF | 12-04-91-C-B | Gen 2 | OligodT/OligodT Purified | GE Oligo dT illustra mRNA kit | 350 | 5.98 | 17.6 | Highly Contaminated |
| 5 | GCSF | 12-04-107-C | Gen 2 | Oligo dT purified (contaminated Feedstock) | GE Oligo dT illustra mRNA kit | 217 | >10 | >46 | Highly Contaminated |
| 6 | GCSF | 12-04-107-C | Gen 2 | Highly contaminated Sample 5 Oligo dT purified using homemade dT resin (1st iteration) | Homemade Oligo dT Sepharose | 386 | 0.843 | 2.19 | Endotoxin detected |
| 7 | GCSF | 12-04-107-C | Gen 2 | Highly contaminated Sample 5 Oligo dT purified using homemade dT resin 2nd iteration of dT | Homemade Oligo dT Sepharose | 102 | <0.100 | <0.12 | Below Detection Limit |
| 8 | GCSF | 12-04-107-C | Gen 2 | Sample 5 dT purification flowthrough fraction (impurity containing) 1st iteration | Homemade Oligo dT Sepharose | 17 | 6.05 | 355.88 | Highly Contaminated |
| 9 | GCSF | 12-04-114-C | Gen 2 | Large Scale homemade oligo dT purification | Homemade Oligo dT Sepharose | 429 | 0.10 | <.23 | Below Detection Limit |
| 10 | GCSF | 12-04-115-C | Gen 2 | Large Scale homemade oligo dT purification | Homemade Oligo dT Sepharose | 322 | 0.10 | <.31 | Below Detection Limit |
| 11 | EPO | 12-01-33-C | Gen 2 | Large Scale homemade oligo dT purification | Homemade Oligo dT Sepharose | 351 | 0.10 | <.28 | Below Detection Limit |
| 12 | GCSF | 12-04-113-C | Gen 2 | Large Scale homemade oligo dT purification | Homemade Oligo dT Sepharose | 399 | 0.10 | <0.25 | Below Detection Limit |

Figure 7

| dT Purification Run | Recovered mg) | Loaded (mg) | Recovery (%) |
|---|---|---|---|
| Run 1 | 72 | 84 | 86 |
| Run 2 | 82 | 84 | 98 |
| Run 3 | 82 | 84 | 98 |
| Run 4 | 69 | 77 | 90 |
| Composite | 305 | 329 | 93 |

Figure 14

| Sample | % ligand bound during coupling | Binding capacity (mg RNA/mL) |
|---|---|---|
| 20mer dT (7mg ligand/mL resin) | 66 | 1.60 |
| 20mer dT (15mg ligand/mL resin) | 18 | 1.57 |
| 50mer dT (7mg ligand/mL resin) | 78 | 1.17 |
| 50mer dT (15mg ligand/mL resin) | 33 | 1.17 |

Figure 16

RIBONUCLEIC ACID PURIFICATION

CROSS REFERENCE TO RELATED APPLICATIONS

This application is a continuation of U.S. application Ser. No. 14/776,864, filed Sep. 15, 2015, which is a 35 U.S.C. § 371 U.S. National Stage Entry of International Application No. PCT/US2014/026842, filed Mar. 13, 2014, which claims the priority of U.S. Provisional Patent Application No. 61/734,842, filed Mar. 15, 2013, the contents of each of which are herein incorporated by reference in its entirety.

BACKGROUND

Commercially-available resins having polythymidine oligonucleotide ligands typically contain less than 30 thymidine (2'deoxy) residues and some commercial resin suppliers utilize a distribution of dT chain lengths, not of a discreet length. Commercially-available oligo dT resins are predominantly kit-based and are typically utilized for small scale (<1 mg) mRNA isolations on a bench top from crude cell/tissue extracts or blood. Commercially-available matrices typically consist of cellulose, latex particles, and magnetic beads containing dT ligands. These options are not generally viable for large scale chromatographic processes for cGMP manufacture of therapeutic mRNAs. In particular, cellulose resin produces significant quantities of leached ligand, contains significant amounts of fine particulates, and has poor flow properties; making it less than ideal for column chromatography. In terms of RNA quality and purity, commercially-available, cellulose based media has been found to yield eluted PolyA containing RNA with substantial endotoxin contamination as well as considerable enzyme and DNA template carryover and contamination. RNA produced using this commercially-available cellulose resin must generally be coupled with additional separation procedures to ensure RNA is of acceptable quality for pre-clinical studies and therapeutic use. Endotoxin contamination is detrimental to patient safety and therefore a process that introduces endotoxin into a drug substance is generally not viable for use in patients.

SUMMARY

Disclosed herein is a method for purifying an RNA transcript comprising a polyA tail, the method comprising: a) obtaining a first sample comprising the RNA transcript, wherein the first sample comprises at least 5%, 10%, 20%, 30%, 40%, 50%, 60%, 70%, 80%, 90%, 91%, 92%, 93%, 94%, 95%, 96%, 97%, 98%, or 99% RNA transcript and at least 5%, 10%, 20%, 30%, 40%, 50%, 60%, 70%, 80%, 90%, 91%, 92%, 93%, 94%, 95%, 96%, 97%, 98%, or 99% impurities, and wherein the percentage of RNA transcript and the percentage of impurities are the inverse of each other; b) contacting the first sample with a surface linked to a plurality of thymidines or derivatives thereof and/or a plurality of uracils or derivatives thereof (polyT/U) under conditions such that the RNA transcript binds to the surface; c) eluting the RNA transcript from the surface; and d) collecting the RNA transcript in a second sample, wherein the second sample comprises at least 5%, 10%, 20%, 30%, 40%, 50%, 60%, 70%, 80%, 90%, 91%, 92%, 93%, 94%, 95%, 96%, 97%, 98%, or 99% RNA transcript and no more than less than 1%, 1%, 2%, 3%, 4%, 5%, 10%, 20%, 30%, 40%, 50%, 60%, 70%, 80%, 90%, 91%, 92%, 93%, 94%, 95%, 96%, 97%, 98%, or 99% impurities, and wherein the percentage of RNA transcript and the percentage of impurities are the inverse of each other.

In some aspects, the method further comprises washing the surface with a solution after step b). In some aspects, the method further comprises preheating the first sample before step b). In some aspects, one or more steps are performed using a batch process.

In some aspects, the sample comprises DNA and the sample has not been subjected to DNase treatment. In some aspects, the one or more impurities comprise an RNA that does not comprise a polyA tail, a deoxyribonucleic acid (DNA), a carbohydrate, a toxin, a polypeptide, and/or a nucleotide. In some aspects, the DNA is plasmid DNA. In some aspects, the DNA is polymerase chain reaction (PCR) product DNA. In some aspects, the DNA comprises non-amplified DNA template. In some aspects, the toxin is lipopolysaccharide (LPS). In some aspects, the toxin is an endotoxin.

In some aspects, the surface is a resin. In some aspects, the surface comprises sepharose. In some aspects, the surface comprises agarose. In some aspects, polyT/U is 5 to 200 thymidines and/or uracils in length or 10 to 50 thymidines and/or uracils in length. In some aspects, polyT/U is 20 thymidines in length. In some aspects, polyT/U is linked directly to the surface. In some aspects, polyT/U is linked to the surface via a linker.

In some aspects, the contacting step is performed at a temperature of 65° C. In some aspects, the contacting step is performed at a rate of 100 cm/h.

In some aspects, the RNA transcript and polyT/U bind one another via non-covalent bonding. In some aspects, the first sample comprises a salt solution. In some aspects, the first sample comprises a sodium chloride solution.

In some aspects, the washing step comprises applying one or more solutions comprising a salt. In some aspects, the salt is NaCl or KCl.

In some aspects, the washing step comprises applying a first salt buffer and a second salt buffer, wherein the first salt buffer has a higher salt concentration than the second salt buffer, and wherein the first salt buffer is applied before the second salt buffer. In some aspects, first salt buffer comprises 0.5M NaCl, 10 mM Tris, and 1 mM EDTA, and has a pH of 7.4. In some aspects, the second salt buffer comprises 0.1M NaCl, 10 mM Tris, and 1 mM EDTA, and has a pH of 7.4. In some aspects, the first salt buffer is applied to the surface at a temperature of 65° C. or 25° C. In some aspects, the first salt buffer is applied to the surface twice, wherein the first application is at a first temperature of 65° C., and wherein the second application is at a second temperature of 25° C. In some aspects, the second salt buffer is applied to the surface at a temperature of 25° C.

In some aspects, the elution step is performed with an elution buffer. In some aspects, the elution buffer is salt-free. In some aspects, the elution buffer comprises 10 mM Tris and 1 mM EDTA, and has a pH of 7.4. In some aspects, the elution step is performed at a temperature of 65° C.

In some aspects, the RNA transcript is the product of in vitro transcription using a non-amplified DNA template. In some aspects, the RNA transcript is 100 to 10,000 nucleotides in length.

In some aspects, the method is repeated 2, 3, 4, 5, 6, 7, 8, 9, 10, 15, 20, 25, 30, 35, 40, 45, 50, or greater than 50 times with the same surface (or any integer between each of the indicated numeric values).

Also disclosed herein is a composition comprising a surface linked to a plurality of thymidines or derivatives thereof and/or a plurality of uracils or derivatives thereof (polyT/U), wherein the surface comprises a polymer, and wherein polyT/U is linked to the surface by a linker.

In some aspects, the polymer is a crosslinked, beaded-form of a polysaccharide polymer material extracted from seaweed. In some aspects, the polymer comprises agarose. In some aspects, the polymer comprises sepharose.

In some aspects, the linker comprises 5'-hexylamine. In some aspects, the linker is coupled to polyT/U via an amide bond.

In some aspects, polyT/U is 5 to 200 thymidines and/or uracils in length or 10 to 50 thymidines and/or uracils in length. In some aspects, polyT/U is 20 thymidines in length. In some aspects, polyT/U comprises one or more modifications. In some aspects, the modification comprises a 2'-O-methyl modification, a 2'-fluoro modification, or a locked nucleic acid (LNA) modification.

In some aspects, the surface is a resin. In some aspects, the resin has a pore size of 300 to 8000 Angstroms or 1000 to 4000 Angstroms.

In some aspects, the composition can be reused 2, 3, 4, 5, 6, 7, 8, 9, 10, 15, 20, 25, 30, 35, 40, 45, 50, or greater than 50 times (or any integer between each of the indicated numeric values).

Also disclosed herein is a method for making the composition of claim [0013], the method comprising: obtaining a surface attached to a first group; and contacting the surface with a polyT/U attached to a second group, wherein the first group and the second group are reactive with one another upon contact.

In some aspects, the first group is N-hydroxysuccinimidyl (NHS) ester. In some aspects, the second group is an amino group. In some aspects, the amino group is located at the 5' end of polyT/U.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 7 shows endotoxin Levels in mRNA batches following purification using various poly dT resins.

FIG. 14 shows yield data of 4 consecutive large scale purifications of lot 12-04-79-I.

FIG. 16 shows a comparison of 20mer and 50mer polythymidine Sepharose resin.

DETAILED DESCRIPTION

Figure 1A:
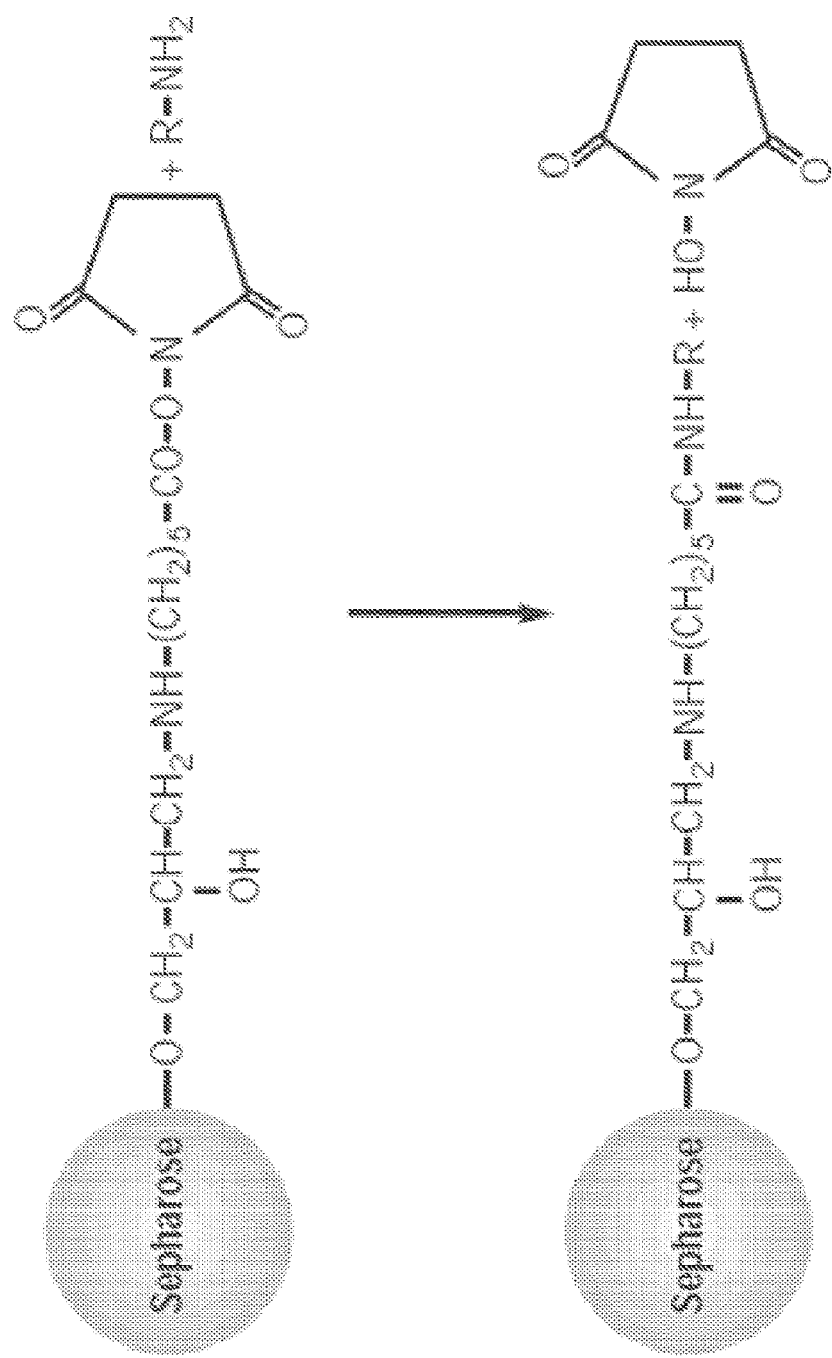
FIG. 1a shows a schematic of poly T/U conjugation to NHS-activated Sepharose resin, where R is poly T/U.

Terms used in the claims and specification are defined as set forth below unless otherwise specified.

Polynucleotide. The term "polynucleotide" is interchangeable with nucleic acid, and includes any compound and/or substance that comprise a polymer of nucleotides. RNA transcripts produced by the method of the invention and DNA templates used in the methods of the invention are polynucleotides. Exemplary polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

RNA transcript. As used herein, an "RNA transcript" refers to a ribonucleic acid produced by an in vitro transcription reaction using a DNA template and an RNA polymerase. As described in more detail below, an RNA transcript typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, modified mRNA "mmRNA" or modified mRNA, and primary construct. Modified RNA, e.g., RNA transcripts, e.g., mRNA, are disclosed in the following which is incorporated by reference for all purposes: U.S. patent application Ser. No. 13/791,922, "MODIFIED POLYNUCLEOTIDES FOR THE PRODUCTION OF BIOLOGICS AND PROTEINS ASSOCIATED WITH HUMAN DISEASE," filed Mar. 9, 2013.

Gene of interest. As used herein, "gene of interest" refers to a polynucleotide which encodes a polypeptide or protein of interest. Depending on the context, the gene of interest refers to a deoxyribonucleic acid, e.g., a gene of interest in a DNA template which can be transcribed to an RNA transcript, or a ribonucleic acid, e.g., a gene of interest in an RNA transcript which can be translated to produce the encoded polypeptide of interest in vitro, in vivo, in situ or ex vivo. As described in more detail below, a polypeptide of interest includes but is not limited to, biologics, antibodies, vaccines, therapeutic proteins or peptides, etc.

DNA template. As used herein, a DNA template refers to a polynucleotide template for RNA polymerase. Typically a DNA template includes the sequence for a gene of interest operably linked to a RNA polymerase promoter sequence.

Operably linked: As used herein, the phrase "operably linked" refers to a functional connection between two or more molecules, constructs, transcripts, entities, moieties or the like. For example, a gene of interest operably linked to an RNA polymerase promoter allows transcription of the gene of interest.

Poly A tail. As used herein, "poly A tail" refers to a chain of adenine nucleotides. The term can refer to poly A tail that is to be added to an RNA transcript, or can refer to the poly A tail that already exists at the 3' end of an RNA transcript. As described in more detail below, a poly A tail is typically 5-300 nucleotides in length.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

It must be noted that, as used in the specification and the appended claims, the singular forms "a," "an" and "the" include plural referents unless the context clearly dictates otherwise.

Compositions

Poly T/U

Described herein are surfaces linked to poly T/U oligonucleotides. The term "poly T/U oligonucleotide" or "poly T/U" or "poly U/T" refers to a nucleic acid comprising a plurality of thymidines and/or uracils, including, but not limited to, a uracil ribonucleic acid (RNA); a thymidine deoxyribonucleic acid (DNA); or a mixed ribonucleotide-deoxyribonucleotide, i.e., the poly T/U oligonucleotide can include ribose or deoxyribose sugars or a mixture of both. Included are analogs thereof and poly T/U of various lengths. Double and single stranded forms of the poly T/U oligonucleotides are provided. In one embodiment, poly T/U is a 20-mer dT oligonucleotide.

The poly T/U oligonucleotide can include other 5-carbon or 6-carbon sugars, such as, for example, arabinose, xylose, glucose, galactose, or deoxy derivatives thereof or other mixtures of sugars.

Poly T/U Lengths

In certain embodiments, the poly T/U oligonucleotide can refer to nucleic acid molecules of 2-2000 nucleotides in length or any integer therein. In one aspect, the length of poly T/U is designed to vary with the length of the target polyA sequence, the specificity required, the reaction and the hybridization and wash conditions. In some aspects, poly T/U can range from about 5 to about 200 bases or from about 15 to about 50 bases. In some aspects, poly T/U can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or greater than 60 bases in length.

Poly T/U Chemistries

In one aspect, one or more bases of poly T/U can be modified. In some aspects, poly T/U can be modified to increase stability of poly T/U. In some aspects, poly T/U can be modified to increase chemical stability of poly T/U. In some aspects, poly T/U can be modified to increase pH stability of poly T/U. In some aspects, poly T/U can be modified to increase thermal stability of poly T/U.

In certain embodiments, the poly T/U oligonucleotide and/or an oligonucleotide sequence complementary to the poly T/U oligonucleotide can comprise a 3'-oligonucleotide modification, a 5'-oligonucleotide modification, a phosphorothioate, an LNA, a PNA, a morpholino, other alternative backbones, or combinations or derivatives thereof. Suitable poly T/U oligonucleotides can be composed of naturally occurring nucleosides adenosine, guanosine, cytidine, thymidine and uridine, modified nucleosides, substituted nucleosides or unsubstituted nucleosides, or combinations thereof. The nucleosides can also be unnatural nucleosides. The nucleosides can be joined by naturally occurring phosphodiester linkages or modified linkages. The nucleosides can also be joined by phosphorothioate linkages or methylphosphonate linkages.

In some aspects, poly T/U can include or be modified with one or more modifications such as: Poly dT (DNA), Poly Uridine (RNA), 2'O-Methyl Uridine RNA (MNA), 2'Fluoro Uridine RNA (FNA), Locked Nucleic Acid (LNA), Peptide Nucleic Acid (PNA), Additional 2' modified RNAs, Carbohydrates or derivatives thereof, or any combination of any of the above chemistries.

In some aspects, the backbone of poly T/U can include phosphate, phoshorothioate, phosphorodithioate, and/or phosphonoacetate.

In some aspects, poly T/U can include pyrimidine derivatives such as thymidine analogs, uridine analogs, and/or heterocycle modifications. In some aspects, poly T/U can include purine derivaties or analogs such as those that help maintain hydrogen bonding patterns with adenosine.

In some aspects, poly T/U can be attached to a linker. In some aspects, the linker can be at the 5' end of poly T/U. In some aspects, the linker can be at the 3' end of poly T/U. In some aspects, the linker can be located internally within poly T/U. Internal linkers can include spacer derivatives with or without modifications or nucleoside derivatives with or without modifications. Linkers are described in more detail herein.

In some aspects, poly T/U can be attached to a spacer. Spacers are described in more detail herein.

Surfaces

Compositions and methods of the invention can use a surface linked to poly T/U. As used herein, the term "surface" refers to a part of a support structure (e.g., a substrate) that is accessible to contact with one or more reagents, poly T/U oligonucleotides, etc. The shape, form, materials, and modifications of the surface can be selected from a range of options depending on the application. In one embodiment, the surface is sepharose. In one embodiment, the surface is agarose.

The surface can be substantially flat or planar. Alternatively, the surface can be rounded or contoured. Exemplary contours that can be included on a surface are wells, depressions, pillars, ridges, channels or the like.

Exemplary materials that can be used as a surface include, but are not limited to acrylics, carbon (e.g., graphite, carbonfiber), cellulose (e.g., cellulose acetate), ceramics, controlled-pore glass, cross-linked polysaccharides (e.g., agarose or SEPHAROSE™), gels, glass (e.g., modified or functionalized glass), gold (e.g., atomically smooth Au(111)), graphite, inorganic glasses, inorganic polymers, latex, metal oxides (e.g., $SiO_2$, $TiO_2$, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON™, optical fiber bundles, organic polymers, paper, plastics, polacryloylmorpholide, poly(4-methylbutene), polyethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON™. A single material or mixture of several different materials can form a surface useful in the invention.

In some aspects, a surface comprises a polymer.

In some aspects, a surface comprises Sepharose™. An example is shown below, where n is any positive integer:

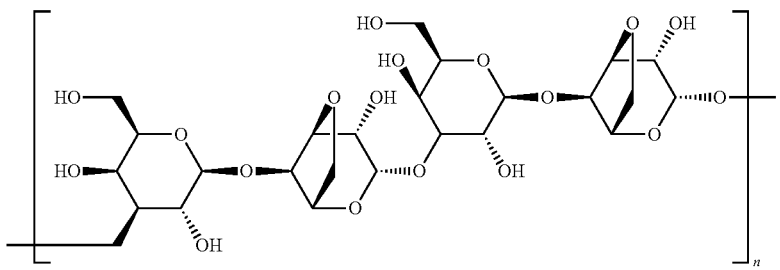

In some aspects, a surface comprises agarose. An example is shown below, where n is a positive integer:

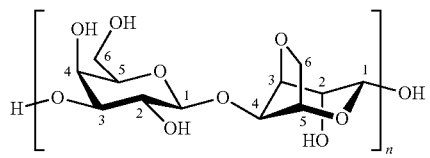

Structure of agarose: D-galactose and 3,6-anhydro-α-L-galactopyranose repeating Unit.

In some aspects, a surface comprises a Polystyrene based polymer. A Polystyrene divinyl benzene copolymer synthesis schematic is shown below:

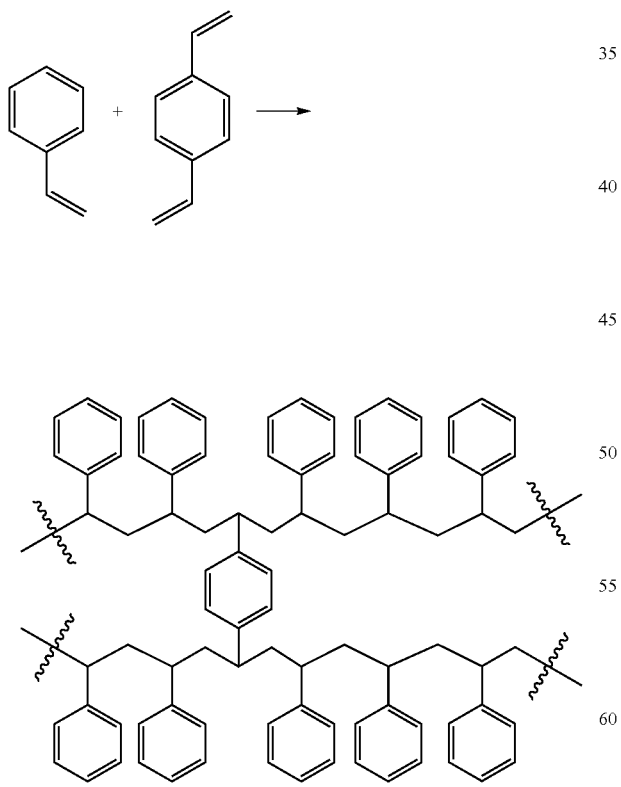

In some aspects, a surface comprises an Acrylic based polymer. Poly (methylmethacrylate) is an example shown below, wherein n is any positive integer:

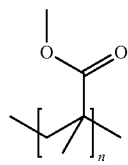

In some aspects, a surface comprises a Dextran based polymer. A Dextran example is shown below:

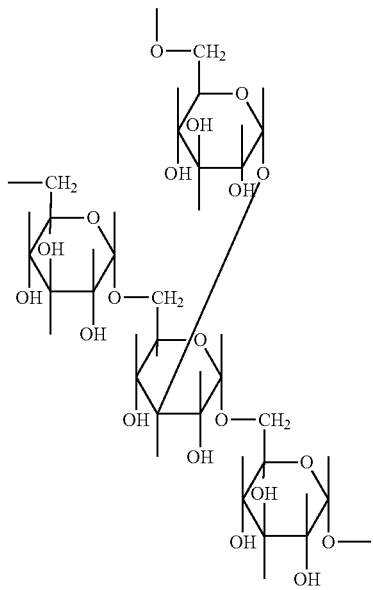

In some aspects, a surface comprises silica. An example is shown below:

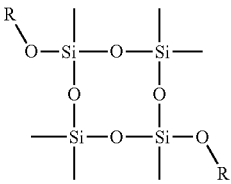

In some aspects, a surface comprises a polyacrylamide. An example cross-linked to N—N-methylenebisacrylamide is shown below:

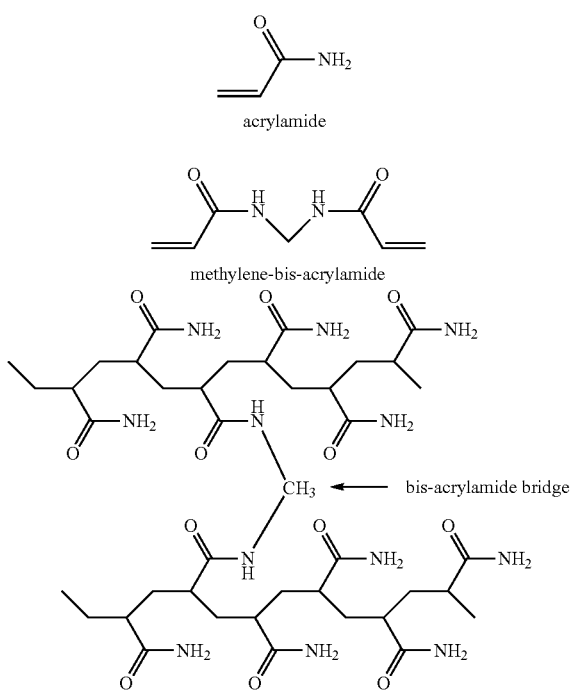

In some aspects, a surface comprises tentacle based phases, e.g., methacrylate based.

A number of surfaces known in the art are suitable for use with the methods of the invention. Suitable surfaces comprise materials including but not limited to borosilicate glass, agarose, sepharose, magnetic beads, polystyrene, polyacrylamide, membranes, silica, semiconductor materials, silicon, organic polymers, ceramic, glass, metal, plastic polycarbonate, polycarbonate, polyethylene, polyethyleneglycol terephthalate, polymethylmethacrylate, polypropylene, polyvinylacetate, polyvinylchloride, polyvinylpyrrolidinone, and soda-lime glass.

In one embodiment, the surface is modified to contain channels, patterns, layers, or other configurations (e.g., a patterned surface). The surface can be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The surface can be a singular discrete body (e.g., a single tube, a single bead), any number of a plurality of surface bodies (e.g., a rack of 10 tubes, several beads), or combinations thereof (e.g., a tray comprises a plurality of microtiter plates, a column filled with beads, a microtiter plate filed with beads).

In some aspects, a surface can include a membrane based resin matrix. In some aspects, a surface can include a resin such as a porous resin or a non-porous resin. Examples of porous resins can include: Additional Agarose based resins (e.g., Cyanogen bromide activated sepharose (GE); WorkBeads™ 40 ACT and WorkBeads 40/10000 ACT (Bioworks)), Methacrylate: (Tosoh 650M derivatives etc.), Polystyrene Divinylbenzene (Life Tech Poros media/GE Source media), Fractogel, Polyacrylamide, Silica, Controlled pore glass, Dextran derivatives, Acrylamide derivatives, and/or Additional polymers; or any combination thereof.

In some aspects, a surface can include one or more pores. In some aspects, pore sizes can be from 300 to 8,000 Angstroms, e.g., 500 to 4,000 Angstroms in size.

In some aspects, a surface can include one or more particles. Examples of particle sizes are 5 um-500 um, 20 um-300 um, and 50 um-200 um. In some aspects, particle size can be 50, 60, 70, 80, 90, 100, 110, 120, 130, 140, 150, 160, 170, 180, 190, or 200 um.

Poly T/U can be immobilized, coated on, bound to, stuck, adhered, or attached to any of the forms of surfaces described herein (e.g., bead, box, column, cylinder, disc, dish (e.g., glass dish, PETR1 dish), fiber, film, filter, microtiter plate (e.g., 96-well microtiter plate), multi-bladed stick, net, pellet, plate, ring, rod, roll, sheet, slide, stick, tray, tube, or vial).

In one embodiment, the surface is modified to contain chemically modified sites that can be used to attach, either covalently or non-covalently, poly T/U to discrete sites or locations on the surface. "Chemically modified sites" in this context includes, but is not limited to, the addition of a pattern of chemical functional groups including amino groups, carboxy groups, oxo groups and thiol groups, that can be used to covalently attach poly T/U, which generally also contain corresponding reactive functional groups. Examples of surface functionalizations are: Amino derivatives, Thiol derivatives, Aldehyde derivatives, Formyl derivatives, Azide Derivatives (click chemistry), Biotin derivatives, Alkyne derivatives, Hydroxyl derivatives, Activated hydroxyls or derivatives, Carboxylate derivatives, activated carboxylate derivates, Activated carbonates, Activated esters, NHS Ester (succinimidyl), NHS Carbonate (succinimidyl), Imidoester or derivated, Cyanogen Bromide derivatives, Maleimide derivatives, Haloacteyl derivatives, Iodoacetamide/iodoacetyl derivatives, Epoxide derivatives, Streptavidin derivatives, Tresyl derivatives, Diene/conjugated diene derivatives (diels alder type reaction), Alkene derivatives, Substituted phosphate derivatives, Bromohydrin/halohydrin, Substituted disulfides, Pyridyl-disulfide Derivatives, Aryl azides, Acyl azides, Azlactone, Hydrazide derivatives, Halobenzene derivatives, Nucleoside derivatives, Branching/multi functional linkers, Dendrimeric funcationalities, and/or Nucleoside derivatives; or any combination thereof.

In some aspects, a surface is linked to poly T/U. In some aspects, the binding capacity of the linked surface can be, e.g., >1 mg/mL, >5 mg/mL, >10 mg/mL, >20 mg/mL, >30 mg/mL, or >40 mg/mL.

Linkers

In some aspects, a surface and/or poly T/U can be attached to a linker. The term "linker" can refer to a connection between two molecules or entities, for example, the connection between poly T/U and a spacer or the connection between poly T/U and a surface (e.g., a 5' hexylamine linker). The linker can be formed by the formation of a covalent bond or a non-covalent bond. Suitable covalent linkers can include, but are not limited to the formation of an amide bond, an oxime bond, a hydrazone bond, a triazole bond, a sulfide bond, an ether bond, an enol ether bond, an ester bond, or a disulfide bond.

A "linker" can refer to either the two or more groups present prior to contact between the groups (e.g. linker precursor groups); or the new group(s) or bond(s) formed after contact between the two or more groups (e.g., linker group(s)). See "Surface synthesis" section for examples of linkers (e.g., first group, second group, bond) and various reaction schemes.

In some aspects, the linker is a 5'-hexylamine linker. In some aspects, the 5'-hexylamine linker can be formed as shown below, where n is any positive integer, e.g., 5 to 500. For example, n is 19 for a 20-mer; and n is 49 for a 50-mer.

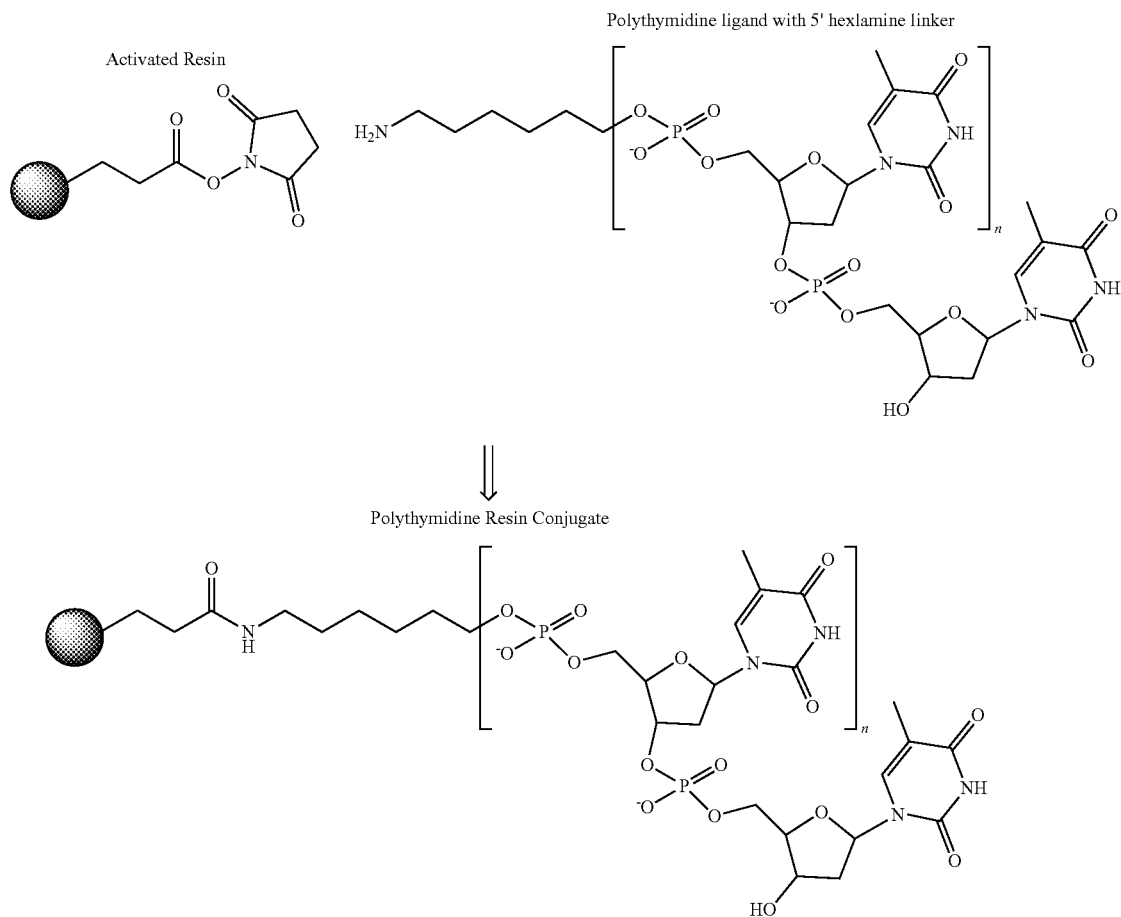

In some embodiments, linkers can optionally be included at a variety of positions within or on poly T/U and/or a surface. Suitable linkers include alkyl and aryl groups, including heteroalkyl and heteroaryl, and substituted derivatives of these. In some instances, linkers can be amino acid based and/or contain amide linkages. Examples of linkers are: Amino derivatives, Thiol derivatives, Aldehyde derivatives, Formyl derivatives, Azide Derivatives (click chemistry), Biotin derivatives, Alkyne derivatives, Hydroxyl derivatives, Activated hydroxyls or derivatives, Carboxylate derivatives, activated carboxylate derivates, Activated carbonates, Activated esters, NHS Ester (succinimidyl), NHS Carbonate (succinimidyl), Imidoester or derivated, Cyanogen Bromide derivatives, Maleimide derivatives, Haloacteyl derivatives, Iodoacetamide/iodoacetyl derivatives, Epoxide derivatives, Streptavidin derivatives, Tresyl derivatives, Diene/conjugated diene derivatives (diels alder type reaction), Alkene derivatives, Substituted phosphate derivatives, Bromohydrin/halohydrin, Substituted disulfides, Pyridyldisulfide Derivatives, Aryl azides, Acyl azides, Azlactone, Hydrazide derivatives, Halobenzene derivatives, Nucleoside derivatives, Branching/multi functional linkers, Dendrimeric funcationalities, and/or Nucleoside derivatives; or any combination thereof.

Spacers

A surface can include a spacer in addition to or instead of a linker. Spacers can include atoms such as carbon or molecules, e.g., carbohydrates, nucleic acids such as DNA or RNA, and/or amino acids; or combinations or analogs thereof. In some aspects, spacers can range from about 5 to about 200 atoms or from about 15 to about 50 atoms. In some aspects, spacers can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms in length.

Methods

RNA Purification

Also disclosed herein are methods for purifying RNA comprising polyA. In some aspects, a method for purifying an RNA transcript comprising a polyA tail includes obtaining a first sample comprising the RNA transcript, wherein the first sample comprises at least 5%, 10%, 20%, 30%, 40%, 50%, 60%, 70%, 80%, 90%, 91%, 92%, 93%, 94%, 95%, 96%, 97%, 98%, or 99% RNA transcript and at least 5%, 10%, 20%, 30%, 40%, 50%, 60%, 70%, 80%, 90%, 91%, 92%, 93%, 94%, 95%, 96%, 97%, 98%, or 99% impurities; contacting the first sample with a surface linked to a plurality of thymidines or derivatives thereof and/or a plurality of uracils or derivatives thereof (polyT/U) under conditions such that the RNA transcript binds to the surface; eluting the RNA transcript from the surface; and collecting the RNA transcript in a second sample, wherein the second sample comprises at least 5%, 10%, 20%, 30%, 40%, 50%, 60%, 70%, 80%, 90%, 91%, 92%, 93%, 94%, 95%, 96%, 97%, 98%, or 99% RNA transcript and no more less than 1%, 2%, 3%, 4%, 5%, 10%, 20%, 30%, 40%, 50%, 60%, 70%, 80%, 90%, 91%, 92%, 93%, 94%, 95%, 96%, 97%, 98%, or 99% impurities.

In some aspects, the method can further includes washing the surface with a solution after the contacting step. In some aspects, the method can further include preheating the first sample before the contacting step. In some aspects, preheating can be at a temperature of 25, 35, 45, 55, 65, 70, 75, 80, 85, or 90° C.

In some aspects, one or more steps of the method are performed using a batch process. In some aspects, one or more steps of the method are performed using a column. In some aspects, the column can be heated and/or jacketed.

In some aspects, the first sample comprises DNA and the sample has not been subjected to DNase treatment. In some aspects, the one or more impurities comprise an RNA that does not comprise a polyA tail, a deoxyribonucleic acid (DNA), a carbohydrate, a toxin, a polypeptide, and/or a nucleotide. In some aspects, the DNA is plasmid DNA. In some aspects, the DNA is polymerase chain reaction (PCR) product DNA. In some aspects, the DNA comprises non-amplified DNA template. In some aspects, the toxin is lipopolysaccharide (LPS). In some aspects, the toxin is an endotoxin.

In some aspects, the surface is a resin. In some aspects, the surface comprises sepharose and/or agarose. In some aspects, polyT/U is 5 to 200 thymidines and/or uracils in length or 10 to 50 thymidines and/or uracils in length. In some aspects, polyT/U is 20 thymidines in length. In some aspects, polyT/U is linked directly to the surface. In some aspects, polyT/U is linked to the surface via a linker. Examples of linkers that can be used for linking are: Amino derivatives, Thiol derivatives, Aldehyde derivatives, Formyl derivatives, Azide Derivatives (click chemistry), Biotin derivatives, Alkyne derivatives, Hydroxyl derivatives, Activated hydroxyls or derivatives, Carboxylate derivatives, activated carboxylate derivates, Activated carbonates, Activated esters, NHS Ester (succinimidyl), NHS Carbonate (succinimidyl), Imidoester or derivated, Cyanogen Bromide derivatives, Maleimide derivatives, Haloacteyl derivatives, Iodoacetamide/iodoacetyl derivatives, Epoxide derivatives, Streptavidin derivatives, Tresyl derivatives, Diene/conjugated diene derivatives (diels alder type reaction), Alkene derivatives, Substituted phosphate derivatives, Bromohydrin/halohydrin, Substituted disulfides, Pyridyl-disulfide Derivatives, Aryl azides, Acyl azides, Azlactone, Hydrazide derivatives, Halobenzene derivatives, Nucleoside derivatives, Branching/multi functional linkers, Dendrimeric functionalities, and/or Nucleoside derivatives; or any combination thereof.

In some aspects, the contacting step is performed at a temperature of 65° C. In some aspects, the contacting step is performed at 4 to 90C. In some aspects, the contacting step is performed at 20 to 70C. In some aspects, the contacting step is performed at 4, 25, 35, 45, 55, 65, 70, 75, 80, 85, or 90C.

In some aspects, the contacting step is performed at a rate of 100 cm/h. In some aspects, the contacting step is performed at a rate of 5 to 7000 cm/h, e.g., 50 to 500 cm/h. In some aspects, the contacting step can be performed in a recirculation mode.

In some aspects, the contacting step is performed using a batch process.

In some aspects, the RNA transcript and polyT/U bind one another via non-covalent bonding. In some aspects, the solution comprising the RNA transcript comprises salt during the contacting step with the surface. Salts are described herein.

In some aspects, the first sample comprises a salt solution. In some aspects, the salt concentration is 0.1-5M, 0.3-2.5M, or 0.5-1M. In some aspects, the salt is a sodium salt, e.g., NaCl. In some aspects, the salt is potassium salt, lithium salt, magnesium salt, calcium salt, and/or ammonium salt. In some aspects, the first sample comprises a sodium chloride solution.

In some aspects, the method can further includes washing the surface with a solution after the contacting step.

In some aspects, the washing step comprises applying one or more solutions comprising a salt. In some aspects, the salt is NaCl or KCl. In some aspects, the salt is NaCl. In some aspects, the salt can be sodium salts, potassium salts, magnesium salts, lithium salts, calcium salts, manganese salts, cesium salts, ammonium salts, and/or alkylammonium salts. In some aspects, the salt can be NaCl, KCl, MgCl2, Ca2+, MnCl2, and/or LiCl.

In some aspects, the washing step comprises applying a first salt buffer and a second salt buffer, wherein the first salt buffer has a higher salt concentration than the second salt buffer, and wherein the first salt buffer is applied before the second salt buffer. In some aspects, the first salt buffer comprises 0.5M NaCl, 10 mM Tris, and 1 mM EDTA, and has a pH of 7.4. In some aspects, the pH can be 4 to 9, e.g., 6 to 8. In some aspects, the second salt buffer comprises 0.1M NaCl, 10 mM Tris, and 1 mM EDTA, and has a pH of 7.4. In some aspects, the pH can be 4 to 9, e.g., 6 to 8. In some aspects, the first salt buffer is applied to the surface at a temperature of 65° C. or 25° C. In some aspects, the temperature can be 4 to 85C. In some aspects, the first salt buffer is applied to the surface twice, wherein the first application is at a first temperature of 65° C., and wherein the second application is at a second temperature of 25° C. In some aspects, the second salt buffer is applied to the surface at a temperature of 25° C. In some aspects, the temperature can be 4 to 85C.

In some aspects, the elution step is performed with an elution buffer. In some aspects, the elution buffer is salt-free. In some aspects, the elution buffer comprises 10 mM Tris and 1 mM EDTA, and has a pH of 7.4. In some aspects, the elution buffer comprises water. In some aspects, the elution buffer comprises a low ionic strength un-buffered salt solution. In some aspects, the elution buffer comprises a low ionic strength buffered salt solution.

Examples of buffers that can be used are shown below in Table A. For example the buffers shown in Table A can be used in one or more elution buffers, first salt buffers, second salt buffers, and solutions used during the contacting step.

TABLE A

| Buffer | pKa 25° C. | pH range |
| --- | --- | --- |
| ACES | 6.78 | 6.1-7.5 |
| acetate | 4.76 | 3.6-5.6 |
| ADA | 6.59 | 6.0-7.2 |
| AMP (2-amino-2-methyl-1-propanol) | 9.69 | 8.7-10.4 |
| AMPD (2-amino-2-methyl-1,3-propanediol) | 8.80 | 7.8-9.7 |
| AMPSO | 9.00 | 8.3-9.7 |
| BES | 7.09 | 6.4-7.8 |
| BICINE | 8.26 | 7.6-9.0 |
| bis-tris | 6.46 | 5.8-7.2 |
| BIS-TRIS propane | 6.80, 9.00 | 6.3-9.5 |
| borate | 9.23, 12.74, 13.80 | 8.5-10.2 |
| cacodylate | 6.27 | 5.0-7.4 |
| carbonate (pK1) | 6.35 | 6.0-8.0 |
| carbonate (pK2) | 10.33 | 9.5-11.1 |
| CHES | 9.50 | 8.6-10.0 |
| citrate (pK1) | 3.13 | 2.2-6.5 |
| citrate (pK2) | 4.76 | 3.0-6.2 |
| citrate (pK3) | 6.40 | 5.5-7.2 |

TABLE A-continued

| Buffer | pKa 25° C. | pH range |
|---|---|---|
| DIPSO | 7.52 | 7.0-8.2 |
| EPPS, HEPPS | 8.00 | 7.6-8.6 |
| ethanolamine | 9.50 | 6.0-12.0 |
| formate | 3.75 | 3.0-4.5 |
| glycine (pK1) | 2.35 | 2.2-3.6 |
| glycine (pK2) | 9.78 | 8.8-10.6 |
| glycylglycine (pK1) | 3.14 | 2.5-3.8 |
| glycylglycine (pK2) | 8.25 | 7.5-8.9 |
| HEPBS | 8.30 | 7.6-9.0 |
| HEPES | 7.48 | 6.8-8.2 |
| HEPPSO | 7.85 | 7.1-8.5 |
| histidine | 1.70, 6.04, 9.09 | 5.5-7.4 |
| hydrazine | 8.10 | 7.5-10.0 |
| imidazole | 6.95 | 6.2-7.8 |
| malate (pK1) | 3.40 | 2.7-4.2 |
| malate (pK2) | 5.13 | 4.0-6.0 |
| maleate (pK1) | 1.97 | 1.2-2.6 |
| maleate (pK2) | 6.24 | 5.5-7.2 |
| MES | 6.10 | 5.5-6.7 |
| MOBS | 7.60 | 6.9-8.3 |
| MOPS | 7.14 | 6.5-7.9 |
| MOPSO | 6.87 | 6.2-7.6 |
| phosphate (pK1) | 2.15 | 1.7-2.9 |
| phosphate (pK2) | 7.20 | 5.8-8.0 |
| phosphate (pK3) | 12.33 | |
| piperazine (pK1) | 5.33 | 5.0-6.0 |
| piperazine (pK2) | 9.73 | 9.5-9.8 |
| piperidine | 11.12 | 10.5-12.0 |
| PIPES | 6.76 | 6.1-7.5 |
| POPSO | 7.78 | 7.2-8.5 |
| propionate | 4.87 | 3.8-5.6 |
| pyridine | 5.23 | 4.9-5.9 |
| pyrophosphate | 0.91, 2.10, 6.70, 9.32 | 7.0-9.0 |
| succinate (pK1) | 4.21 | 3.2-5.2 |
| succinate (pK2) | 5.64 | 5.5-6.5 |
| TABS | 8.90 | 8.2-9.6 |
| TAPS | 8.40 | 7.7-9.1 |
| TAPSO | 7.61 | 7.0-8.2 |
| taurine (AES) | 9.06 | 8.4-9.6 |
| TES | 7.40 | 6.8-8.2 |
| Tricine | 8.05 | 7.4-8.8 |
| triethanolamine (TEA) | 7.76 | 7.0-8.3 |
| Trizma (tris) | 8.06 | 7.5-9.0 |

In some aspects, the elution step is performed at a temperature of 65° C. In some aspects, the elution step is performed at a temperature of 4 to 95C. In some aspects, the elution step is performed at a temperature of 25 to 80C. In some aspects, the elution step is performed at a temperature of 45 to 70C.

In some aspects, the RNA transcript is the product of in vitro transcription using a non-amplified DNA template. In some aspects, the RNA transcript is 100 to 10,000 nucleotides in length. In some aspects, the RNA transcript is 500 to 4000 nucleotides in length. In some aspects, the RNA transcript is 800 to 3000 nucleotides in length.

Surface Synthesis

Also disclosed herein are methods of surface synthesis and attachment of poly T/U. In some aspects, a method for making a surface includes obtaining a surface attached to a first group; and contacting the surface with a polyT/U attached to a second group, wherein the first group and the second group are reactive with one another upon contact.

In some aspects, the first group is N-hydroxysuccinimidyl (NHS) ester. In some aspects, the first group is NHS carbonate. In some aspects, the second group is an amino group. In some aspects, the amino group is located at the 5' end of polyT/U.

In some aspects, examples of the first group are: Amino derivatives, Thiol derivatives, Aldehyde derivatives, Formyl derivatives, Azide Derivatives (click chemistry), Biotin derivatives, Alkyne derivatives, Hydroxyl derivatives, Activated hydroxyls or derivatives, Carboxylate derivatives, activated carboxylate derivates, Activated carbonates, Activated esters, NHS Ester (succinimidyl), NHS Carbonate (succinimidyl), Imidoester or derivated, Cyanogen Bromide derivatives, Maleimide derivatives, Haloacteyl derivatives, Iodoacetamide/iodoacetyl derivatives, Epoxide derivatives, Streptavidin derivatives, Tresyl derivatives, Diene/conjugated diene derivatives (diels alder type reaction), Alkene derivatives, Substituted phosphate derivatives, Bromohydrin/halohydrin, Substituted disulfides, Pyridyl-disulfide Derivatives, Aryl azides, Acyl azides, Azlactone, Hydrazide derivatives, Halobenzene derivatives, Nucleoside derivatives, Branching/multi functional linkers, Dendrimeric funcationalities, and/or Nucleoside derivatives; or any combination thereof.

In some aspects, examples of the second group are: Amino derivatives, Thiol derivatives, Aldehyde derivatives, Formyl derivatives, Azide Derivatives (click chemistry), Biotin derivatives, Alkyne derivatives, Hydroxyl derivatives, Activated hydroxyls or derivatives, Carboxylate derivatives, activated carboxylate derivates, Activated carbonates, Activated esters, NHS Ester (succinimidyl), NHS Carbonate (succinimidyl), Imidoester or derivated, Cyanogen Bromide derivatives, Maleimide derivatives, Haloacteyl derivatives, Iodoacetamide/iodoacetyl derivatives, Epoxide derivatives, Streptavidin derivatives, Tresyl derivatives, Diene/conjugated diene derivatives (diels alder type reaction), Alkene derivatives, Substituted phosphate derivatives, Bromohydrin/halohydrin, Substituted disulfides, Pyridyl-disulfide Derivatives, Aryl azides, Acyl azides, Azlactone, Hydrazide derivatives, Halobenzene derivatives, Nucleoside derivatives, Branching/multi functional linkers, Dendrimeric funcationalities, and/or Nucleoside derivatives; or any combination thereof.

In some aspects, the first group and the second group react to form a bond. In some aspects the bond is an amide bond.

In some aspects, the first group and the second group can be either of the groups (or the group) shown on the left-hand side of the arrow in the reaction schemes shown/detailed below; and the bond can be the group shown on the right-hand side of the arrow(s) in the reaction schemes shown/detailed below.

Amide (substituted amine+substituted succinimidyl ester yields an amide bond) or (azlactone+amine) or (amine+acyl azide) or (amine+succinic anhydride) or (carboxyl+amine with carbodiimide derivatives). For example:

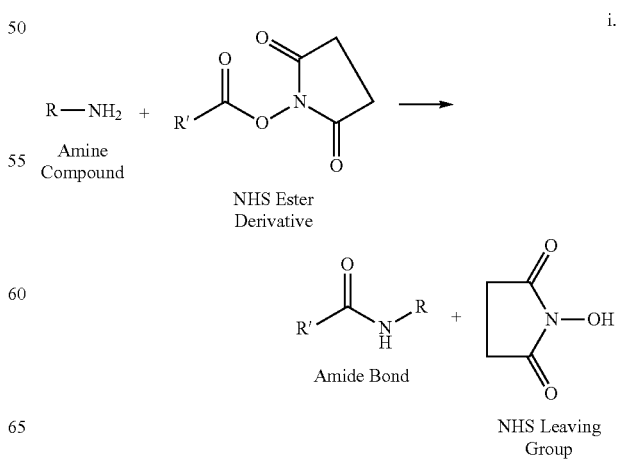

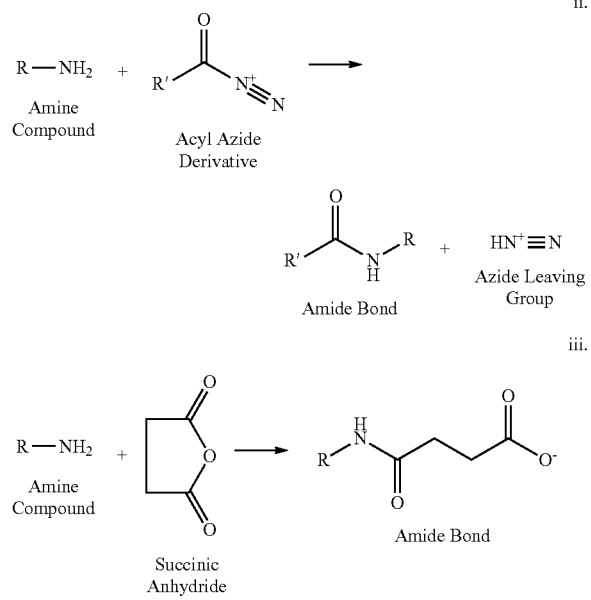
Thioether bond (thiol+maleimide) or (Thiol+haloacetyl) or (thiol+epoxide) or (Halohydrin (ie bromohydrin)+thiol) or (tresyl+thiol) or (thiol+acryloyl derivative) or (sulfhydryl+fluorobenzene derivatives). For example:
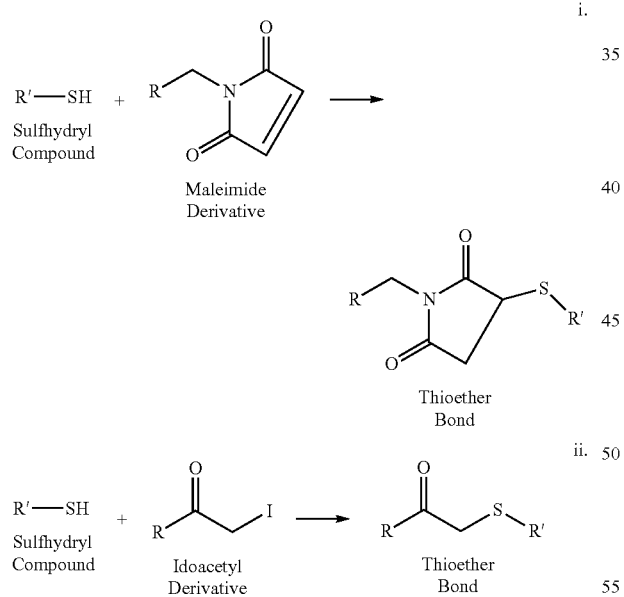
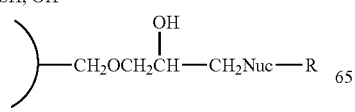
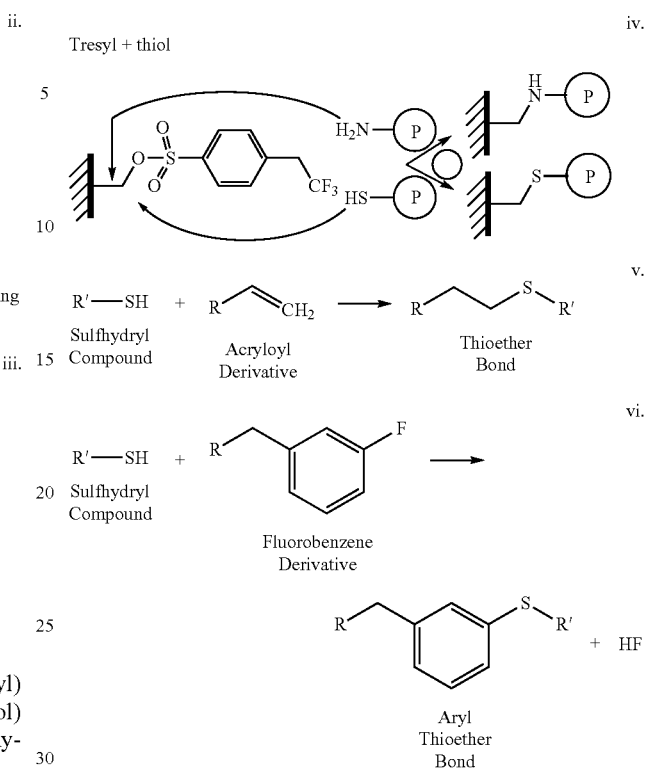
Carbamate (Succinimidyl Carbonate+Amine) or (Carbonyldiimizaole Derivative+Amine). For Example:
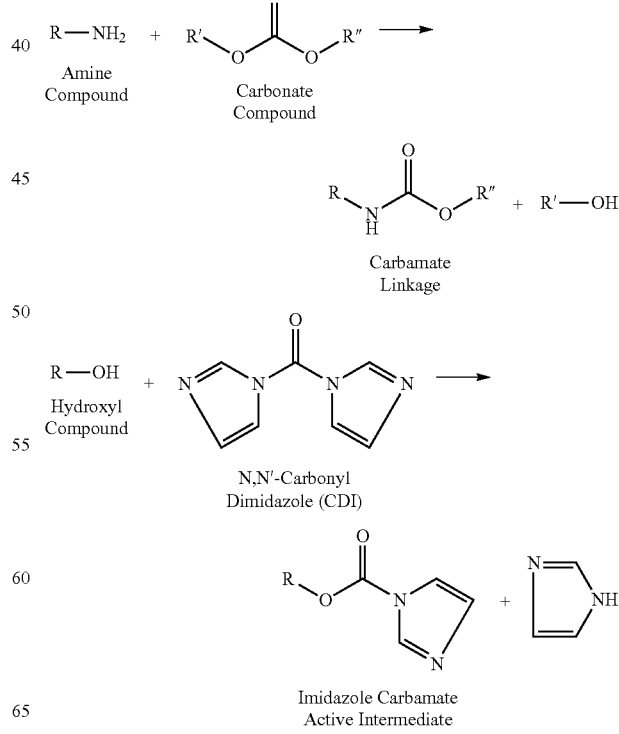

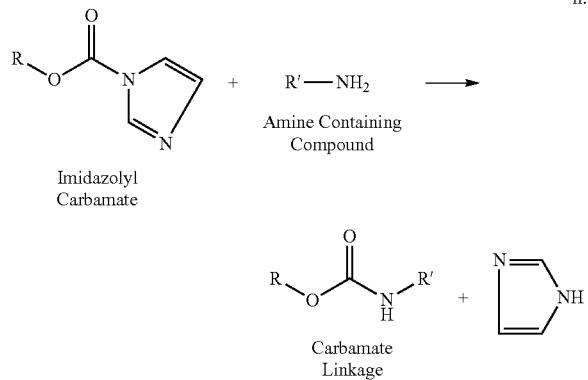

Imidazolyl Carbamate + R'—NH₂ (Amine Containing Compound) → Carbamate Linkage + imidazole Triazole (alkyne+azide (click chemistry)). For example:

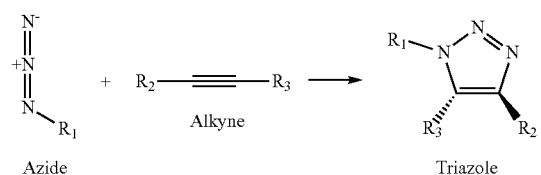

Azide + Alkyne → Triazole

Triazoline (alkene+azide). For example:

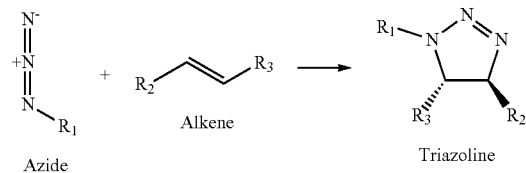

Azide + Alkene → Triazoline

Secondary amine (Aldehyde+amine [reductive amination], or (epoxide+amine) or (Halohydrin (ie bromohydrin)+amine) or (tresyl+amine). For example:

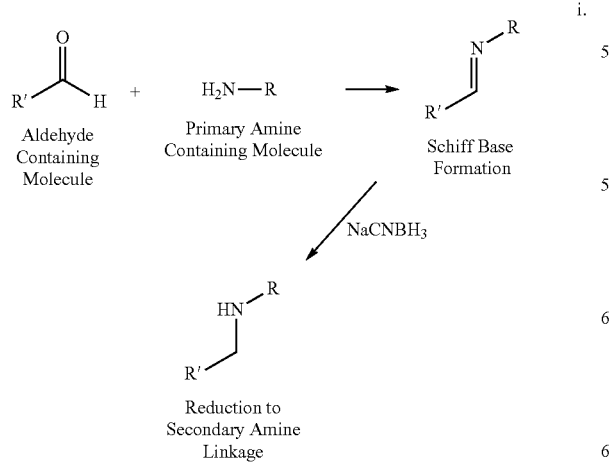

Aldehyde Containing Molecule + Primary Amine Containing Molecule → Schiff Base Formation → (NaCNBH₃) → Reduction to Secondary Amine Linkage ii. Amine + epoxide

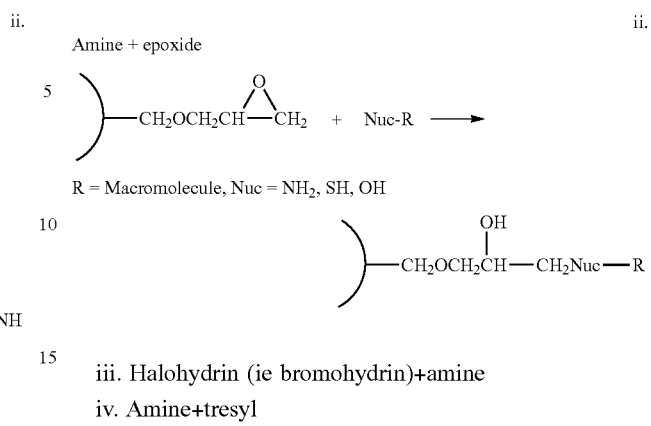

R = Macromolecule, Nuc = NH₂, SH, OH iii. Halohydrin (ie bromohydrin)+amine
iv. Amine+tresyl

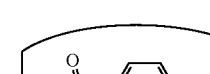

Substituted cyclohexene (conjugated diene+substituted alkene[diels alder reaction]). For example:

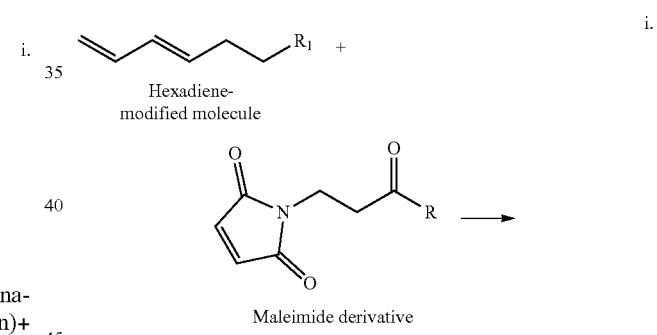

Hexadiene-modified molecule + Maleimide derivative → 2 + 4 Cycloaddition product Hydrazone linkage (hydrazide+aldehyde). For example:

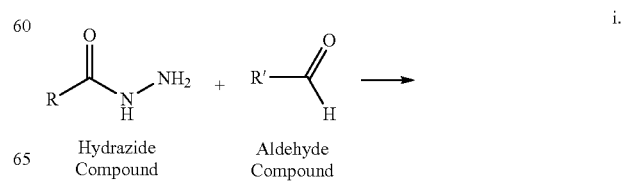

Hydrazide Compound + Aldehyde Compound →

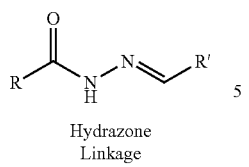

Hydrazone Linkage

Thiourea linkage (isothiocyanate+amine). For example:

i.

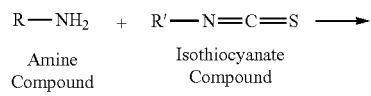

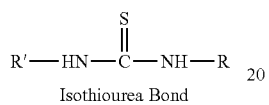

Isothiourea Bond

Ester (hydroxyl+carboxyl (w/1,1-carbonyldiimidazole [CDI])

Substituted disulfide (substituted thiol+pyridal disulfide (aryldisulfide). For example:

i.

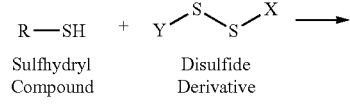

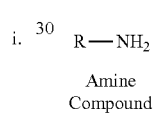

Disulfide Interchange ii.

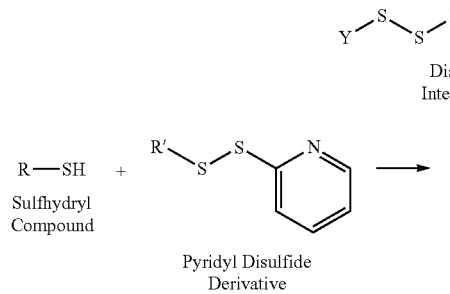

Isourea derivative (cyanogen bromide+amine). For example:

i.

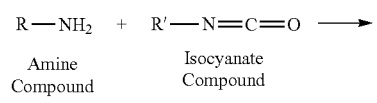

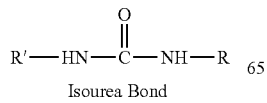

Isourea Bond

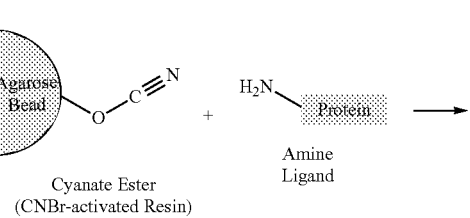

ii.

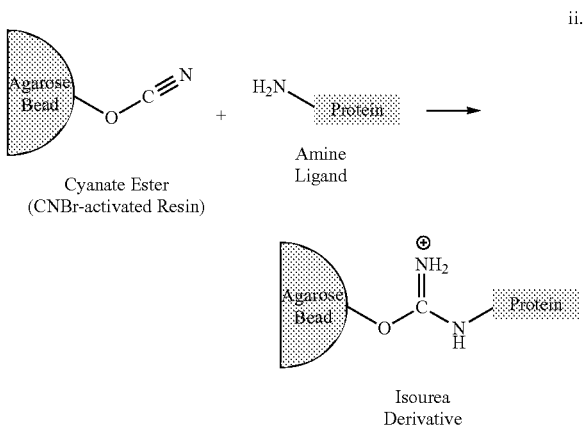

(Strept)avidin/Biotin

Substituted Ether (Halohydrin (ie bromohydrin)+hydroxyl)

Arylamine bond (Amine+fluorobenzene derivative). For example:

i.

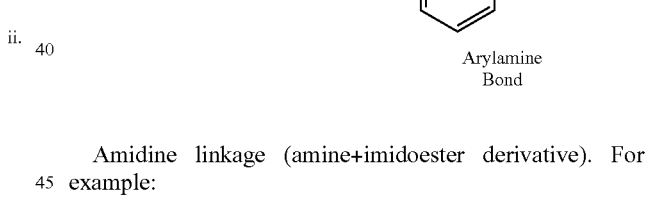

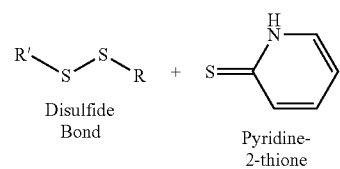

Arylamine Bond

Amidine linkage (amine+imidoester derivative). For example:

i.

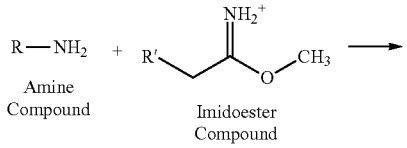

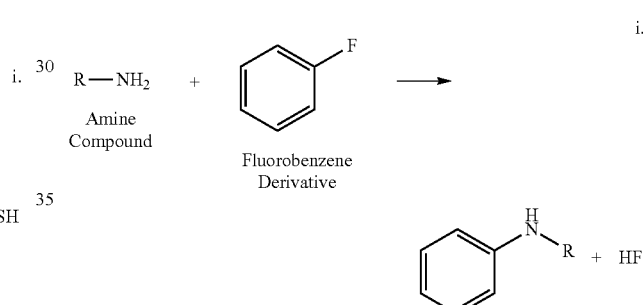

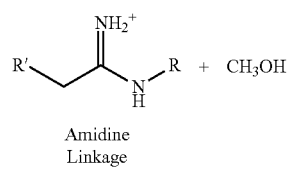

Amidine Linkage

Phosphoramidate bond (alkyl phosphate derivative+amine). For example:

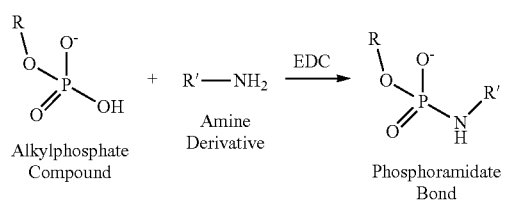

i.

Any use of bifunctional crosslinkers, e.g., Homobifunctional/heterobifunctional, PEG linkers, Peptide linkers, and/or EDC Linkers.

Any use of photochemistry/photoconjugation, e.g., Arylazides and/or Benzophenones.

Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

General Materials and Methods
Resin Synthesis

The purpose of this protocol was to synthesize Oligo dT sepharose resin for use as a medium for affinity based chromatographic purification of polyadenylated mRNA. Bulk NHS activated Sepharose 4 FF was functionalized with a 20mer polythymidine oligonucleotide containing a 5'-hexylamine linker via a stable amide linkage.

Figure 1B:
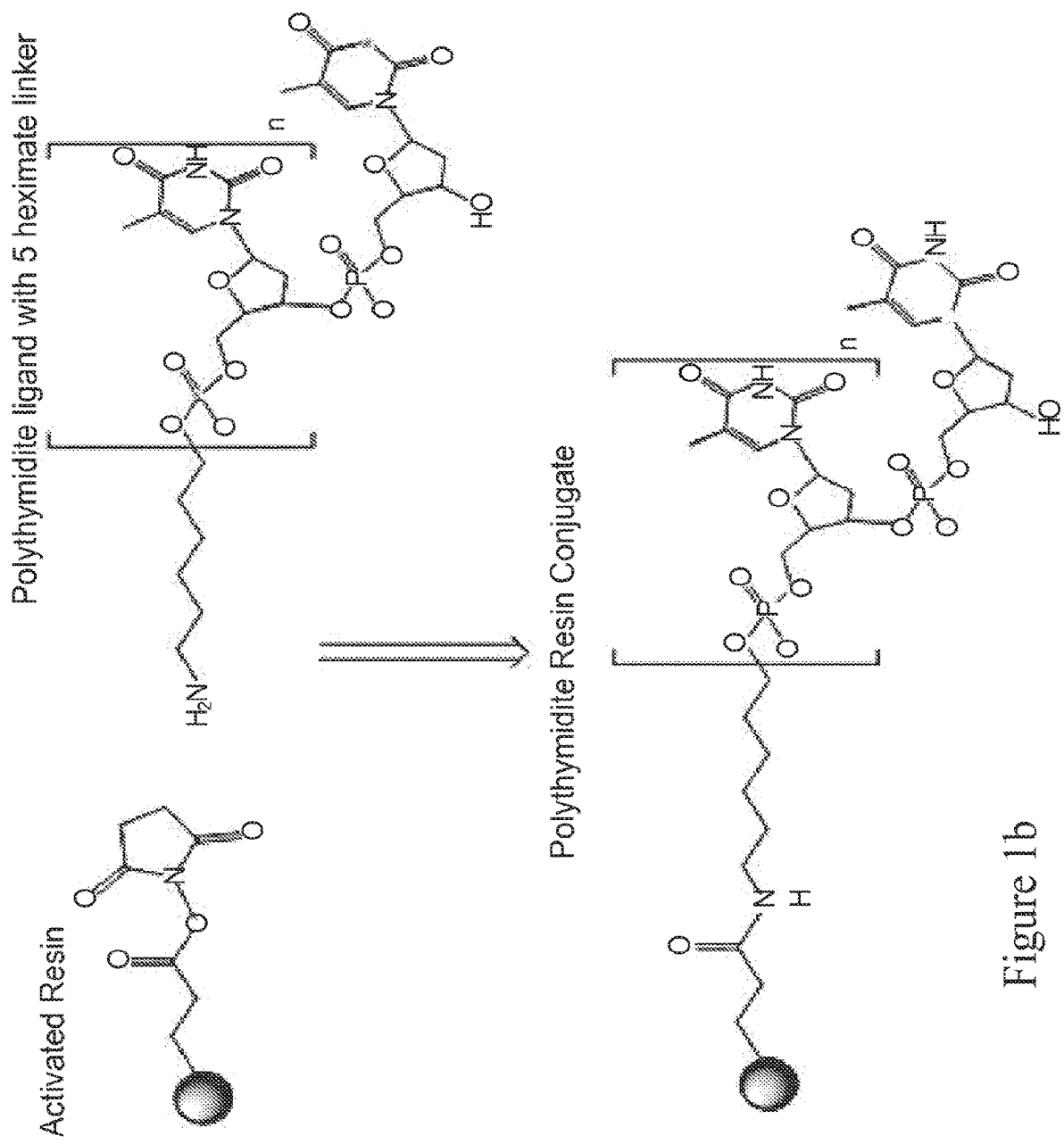
FIG. 1b shows a reaction used to synthesize a poly T/U resin conjugate with a 5'-hexylamine linker connected via a stable amide linkage (n can be any positive integer, e.g., 49 or 19).
Figure 2:
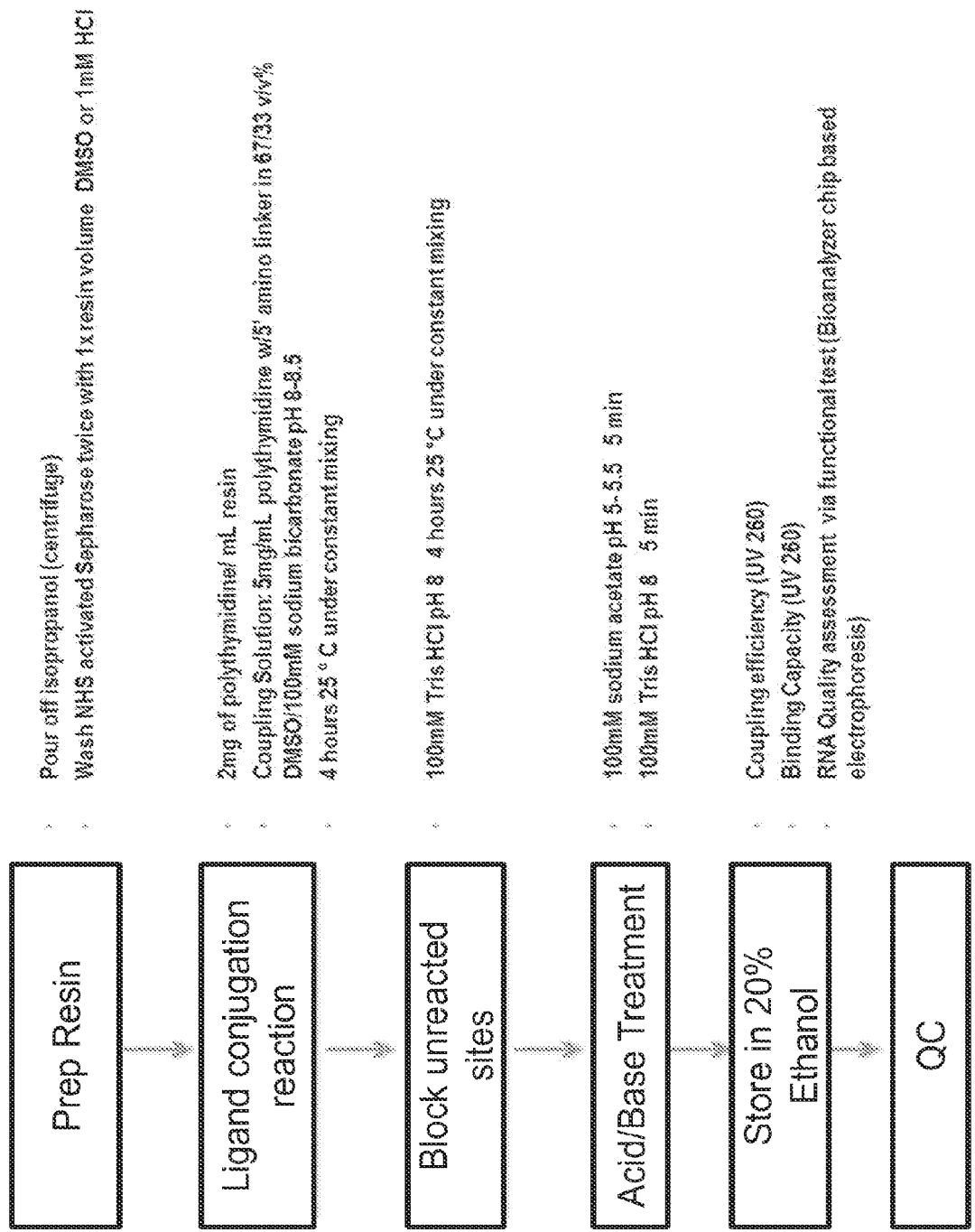
FIG. 2 shows the general resin synthesis process overview.

FIG. 1a shows a schematic of poly T/U conjugation to NHS-activated Sepharose resin. FIG. 1b shows a reaction used to synthesize a poly T/U resin conjugate with a 5'-hexylamine linker via a stable amide linkage (n can be any positive integer, e.g., 49 or 19). FIG. 2 shows the general resin synthesis process overview.

Materials:

| Material | Vendor | Part # |
|---|---|---|
| NHS-Activated Sepharose 4 FF Resin | GE Healthcare | |
| 20mer Polythymidine oligonucleotide with 5' hexylamine linker (HPLC Purified/desalted/lyophilized) Seq: 5'NH2-(C6)-dT- dT- dT- dT- dT- dT- dT- dT- dT- dT- dT- dT- dT- dT- dT- dT- dT- dT- dT- dT- 3' | OligoFactory | |

-continued

| Material | Vendor | Part # |
|---|---|---|
| Stock Solutions | | |
| Dimethylsulfoxide (DMSO) Molecular Biology Grade | Sigma Aldrich | D8418-500 ML |
| Sodium Bicarbonate (NaHCO$_3$), powder, Molecular Biology Grade | Sigma Aldrich | S5761-500G |
| 0.1 M Hydrochloric Acid | Sigma Aldrich | 84434-500 ML |
| 1 M Tris HCl pH 8.0 | Invitrogen | 15568025 |
| 3 M Sodium Actetate (NaOAc) pH 5.5 | Ambion | AM9740 |
| Ethanol, Molecular Biology Grade | Fisher | |
| DNase/RNase free water | MilliQ or Equivalent | |
| Prepared Solutions | | |
| 1mM Hydrochloric Acid 100 mM Tris HCl pH 8 100 mM Sodium Acetate pH 5.5 20% v/v Ethanol 100 mM NaHCO$_3$ 2:1 v/v DMSO: 100 mM NaHCO$_3$ | | |

Preparation of Conjugation Reaction Mixture:

The dry weight to UV weight of dT ligand was obtained. Poly thymidine lyophilized powder was weighed out and dissolved in water (0.5 mg/mL); and then mixed by vortexing. The UV concentration of solution was then obtained on plate reader assuming 1 AU=800 ug/mL (RNA). The dry weight to UV weight conversion was then calculated.

The amount of resin to be made was then determined and the amount of ligand (UV weight) needed to conjugate to resin was calculated. A 100 mM sodium bicarbonate (NaHCO$_3$) solution was prepared with a pH of 8-8.5.

The total amount of dT ligand needed was dissolved (calculated as above and using conversion factor dry weight: UV weight conversion obtained as above) in 100 mM NaHCO$_3$ at a concentration of 15 mg/mL.

Volume of DMSO equivalent to 2×volume of poly dT in 100 mM NaHCO$_3$ solution was added to the 15 mg/mL polydT in 100 mM NaHCO$_3$ (e.g., Add 30 mL DMSO to 15 mL of 15 mg/mL poly dT in 100 mM NaHCO$_3$). Final effective coupling solution was 5 mg/mL polythymidine ligand in 2:1 v/v DMSO:100 mM NaHCO$_3$. UV quantitation on dT solution was then performed.

Resin Conjugation:

The slurry concentration of NHS Sepharose 4FF Resin in isopropanol (IPA) was the determined: Slurry %: Volume of Resin (mL)/Total solution (mL). The resin/IPA mix was then shaken until the slurry was completely homogenous and no resin was deposited at the bottom of the container. In a tube, the homogenous slurry was added and centrifuged at 4000 RPM for 5 min.

The volume of settled resin was recorded after centrifugation and the % slurry calculated. Resin was measured out into appropriate centrifuge compatible, DMSO resistant RXN vessels. A volume of DMSO was added to resin/IPA slurry equivalent to achieve 50% total slurry. Note that in lieu of DMSO, 1 mM HCl can also be substituted to wash resin prior to conjugation.

The resin was centrifuged at 4000 RPM for 5 min and all IPA/DMSO solution was removed. All bulk solution was the poured off and then the remaining residual was poured out.

A volume of DMSO equivalent to the resin volume was added to the settled resin and re-slurried. Resin was centrifuged at 4000 RPM for 5 min and poured off all IPA/DMSO solution as above. This step was then repeated.

The polythymidine conjugation reaction: 5 mg/mL polythymidine in 2:1 DMSO: 100 mM NaHCO$_3$ prepared above was added to resin at a load of 2 mg dT/mL of resin as described above. The reaction mixture was re-slurried until completely homogeneous. The mixture was allowed to react at ambient temperature (20-25° C.) for 2 hours while continuously mixing on an orbital shaker/wave system rocking tray or equivalent. The mixture was centrifuged at 4000 RPM for 10 min and then the reaction mixture was poured off. UV quantitation was then performed on the post conjugation reaction mixture and a mass balance was performed to calculate % dT remaining and effectively % dT coupled to the resin.

Blocking of Unconjugated Sites on Resin:

A volume of 100 mM Tris HCl pH 8 equivalent to the resin volume was added to each tube. Re-slurried the entire mixture until completely homogeneous. The mixture was allowed to react at ambient temperature (20-25° C.) for 2 hours while continuously mixing on an orbital shaker/wave system rocking tray or equivalent. The mixture was then centrifuged at 4000 RPM for 10 min. All bulk solution then poured off.

Acid/Base Treatment:

A volume of 100 mM sodium acetate pH 5.5 equivalent to the resin volume was added to each tube. Re-slurried the entire mixture until completely homogeneous. The homogeneous mixture was then allowed to stand for 2 minutes, then centrifuged at 4000 RPM for 5 min and poured off all bulk solution.

A volume of 100 mM Tris HCl pH8 equivalent to the resin volume was then added to each tube. Re-slurried the entire mixture until completely homogeneous. The homogeneous mixture was allowed to stand for 2 minutes, then centrifuged at 4000 RPM for 5 min and poured off all bulk solution.

Resin Storage:

Where applicable, a volume of 20% ethanol solution equivalent to 0.75×the resin volume was added to each tube. Re-slurried the entire mixture until completely homogeneous. All resin was pooled and mixed for 2 minutes by vigorously shaking. Resin is stored in 20% ethanol at 4° C., as needed.

Quality Control:

Quality control can be performed to ensure that the functionalization of the resin was successful and to determine the binding capacity for the prepared resin lot. The procedure is generally outlined below.

RNA Purification

The purpose of this protocol was to selectively purify polyadenylated mRNA using oligo dT (polythymidine) affinity chromatography resin at small scale using a solid phase extraction vacuum manifold. Short mRNA transcripts, abort sequences, and protein were typically removed as mRNA containing poly A tail is captured on the resin and the aforementioned impurities flow through and do not bind to the resin.

Figure 3:
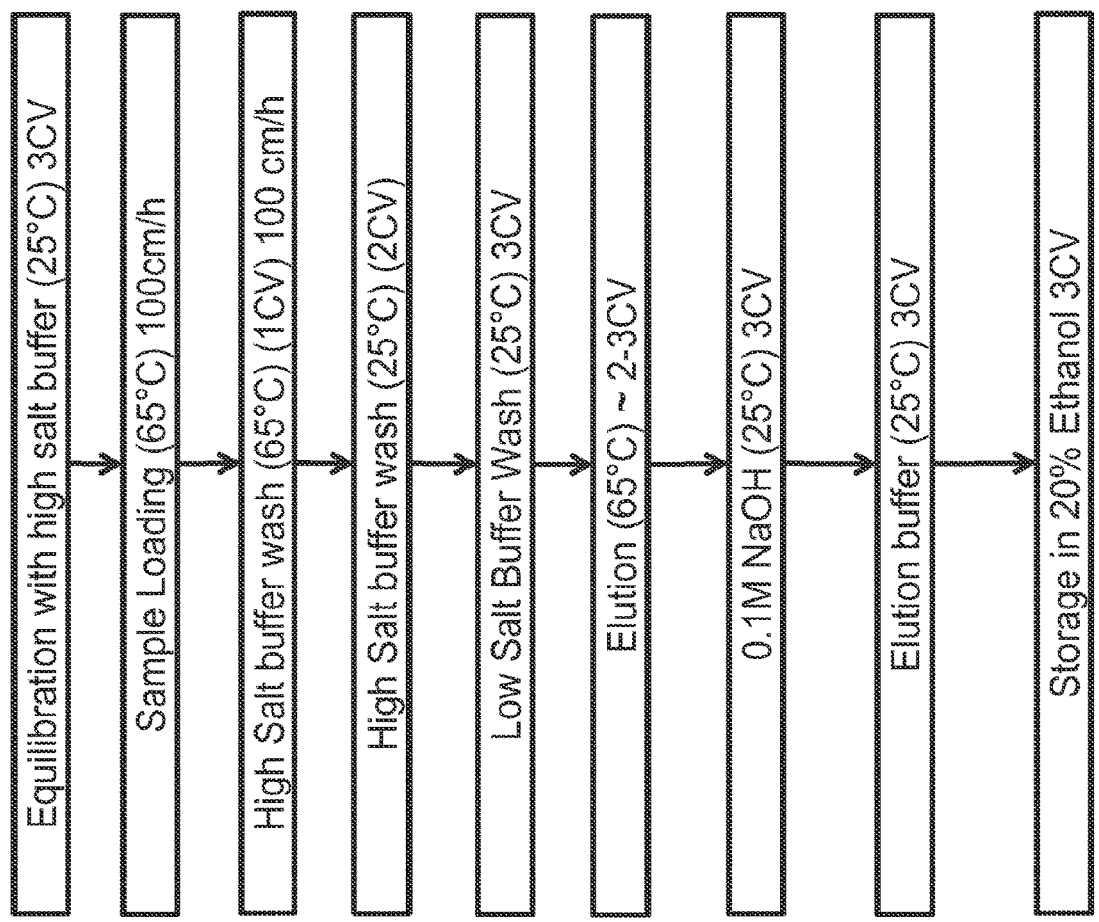
FIG. 3 shows a general overview of the process used to purify polyadenylated RNA.

FIG. 3 shows a general overview of the process used to purify polyadenylated RNA.

Materials:

| Material | Vendor (where applicable) | Part # |
|---|---|---|
| 5 M Sodium chloride (Bioultra) | Sigma | |
| DNase/RNase free water | Teknova or equivalent | |
| 10X Tris EDTA (TE) Buffer (100 mM Tris HCl 10 mM EDTA pH 7.4) | | |
| High Salt Equilibration/Wash Buffer (0.5 M NaCl, 10 mM Tris HCl, 1 mM EDTA pH 7.4) | | |
| 5X Sample Buffer (2.5 M NaCl, 50 mM Tris HCl 5 mM EDTA, pH 7.4) | | |
| Low Salt Wash Buffer (0.1 M NaCl, 10 mM Tris HCl, 1 mM EDTA pH 7.4) | | |
| Elution Buffer (10 mM Tris HCl, 1 mM EDTA pH 7.4) | | |
| Oligo dT Cellulose | Sigma | |
| 20mer Oligo dT Sepharose | | |
| Solid phase extraction columns/ Spin columns | Biotage/Invitrogen | |
| DNase/RNase-free water | Teknova or equivalent | W3350 or equivalent |
| DNase/RNase/pyrogen free certified 200 μL PCR tubes/PCR plates/2.0 mL microfuge tube/15 mL conical tube/50 mL conical tube | | |
| Ethanol (molecular biology grade) | Fisher or equivalent | |
| 0.2 um filter | Millipore or equivalent | |

Procedure:

The amount of oligo dT resin to use for purification was determined and the column was packed. The elution buffer was placed at 65° C. until immediately prior to product elution. mRNA was then prepared to be loaded on dT resin by adding 5×sample buffer to mRNA sample(s) and preheating the mRNA containing solution to 65° C. and heating at 65° C. for 15 min in an oven or for 10 min in a water bath.

The resin was then equilibrated with high salt buffer in one or more columns. If using Sigma resin slurry solid resin in high salt buffer: Add 2-3 column volumes of high salt buffer to the columns and drain liquid in column. Repeat 2×. If using Applicant's dT Sepharose resin slurried in 20% EtOH: Add 2-3 column volumes of high salt buffer to the columns and drain liquid in column. Repeat 2×.

65° C. preheated mRNA solution was added to the resin column, reslurried in mRNA/sample buffer solution and placed at 65° C. for 15 min in an oven or for 10 min in a water bath with periodic shaking. The mRNA/resin solution was placed at ambient temperature (20-25° C.) for 30 minutes while shaking continuously and keeping the resin as a slurry. The liquid in column was drained into a clean centrifuge tube. A volume of high salt buffer equal to 2-3 resin volumes was added to wash the unbound material off of the resin and repeated once. A volume of low salt buffer equal to 2-3 resin volumes was added to wash the unbound material off of the resin and repeated twice. The mRNA full length product (FLP) was eluted using 2-3 resin volumes of 65° C. elution buffer; ensuring a slow flow rate to maximize contact time of 65° C. elution buffer with resin and repeated with 1-2 resin volumes of elution buffer.

UV quantitation was performed on mRNA in the elution fraction and flowthrough/wash fraction to calculate recovery/yield. Bioanalyzer gel analysis was performed on elution fraction (mRNA FLP containing fraction) to ensure electropherogram contains a single discreet peak at the appropriate size with no lower molecular weight impurities.

The mRNA can be diafiltered into water using a UF/TFF step. The mRNA can be diafiltered into water via UF spin filters or TFF prior to lyophilization. All salts are generally removed prior to formulating mRNA into a desired buffer/matrix.

Example 1: Sepharose Resin Preparation and Quality Control

Activated Resin: NHS activated Sepharose FF.

Ligand: The ligand utilized was a 20-mer polythymidine (2'deoxy) oligonucleotide containing a 5' hexylamine linker. The ligand was synthesized using standard solid phase synthesis methods, was chromatographically purified, and lyophilized prior to use.

The 20mer polythymidine ligand (890 mg) was dissolved in a 100 mM sodium bicarbonate solution (pH-8.5) at ~15 mg/mL. Dimethylsulfoxide (DMSO) was added to the ligand containing solution to achieve a final concentration of 5 mg/mL in 67/33 (v/v %) DMSO/100 mM NaHCO$_3$.

Activated resin (425 mL) was centrifuged at 500×g to remove the Isopropanol, re-slurried, washed twice, each time with 1 resin volume equivalent 1 mM HCl for 5 minutes, the resin was centrifuged and HCl was poured off.

Upon complete removal of HCl, all polythymidine oligo solution (5 mg/mL in 67/33 (v/v %) DMSO/100 mM NaHCO$_3$ was added to the resin and re-slurried; the coupling reaction was performed at 25° C. for 4 hours under constant shaking using an orbital shaker to maintain consistent slurry and to prevent resin settling.

The reaction was centrifuged at 500×g and the coupling solution was poured off and quantified by UV absorbance at 260 nm to assess coupling efficiency. It was determined that 99% of starting material had bound to the resin.

To block any remaining unconjugated sites on the resin, the resin was treated with 425 mL of 100 mM Tris HCl pH 8; the mixture was re-slurried and was allowed to react at 25° C. for 4 hours under constant shaking using an orbital shaker to maintain consistent slurry and to prevent resin settling. The reaction was centrifuged at 500×g and the solution was poured off.

The resin was re-slurried and washed with 425 mL of 100 mM sodium acetate solution pH 5 for 5 minutes. The mixture was centrifuged at 500×g and the solution was poured off.

The resin was re-slurried and washed with 425 mL of 100 mM Tris HCl solution pH 8 for 5 minutes. The mixture was centrifuged at 500×g and the solution was poured off.

A 20%/80% water/ethanol (v/v %) solution was added to the resin to achieve a 55% slurry; The resin was re-slurried a final time and was stored at 4° C. This resin is typically referred to as Applicant's dT resin or similar terminology.

Figure 4:
FIG. 4 shows gel electropherograms of binding assessment for 20mer dT Sepharose resin.

For additional quality control (QC), the binding capacity of the resin and the resin's ability to capture poly A containing RNA was tested with an excess of GCSF encoded mRNA lot: "GCSF PD 29" loaded onto a 2.5 mL column packed with the synthesized lot of resin. Binding capacity was determined to be 1.4 mg RNA/mL resin by UV absorbance measurement at 260 nm. RNA of acceptable quality was observed via chip based electrophoresis using a Biorad Experion Bioanalyzer system. The gel electropherogram can be seen in FIG. 4.

Example 2: dT Column Leaching Analysis

Quantitation of total residual thymidine was performed using LC-MS/MS analysis. Purified and capped mRNA was subjected to a nuclease P1 digestion followed by treatment with bovine alkaline phosphatase (BAP). RNA and DNA were digested to individual nucleotides and abundances of each individual nucleotide (from DNA and RNA) were assayed and quantified using tandem mass spectrometry.

Figure 5:
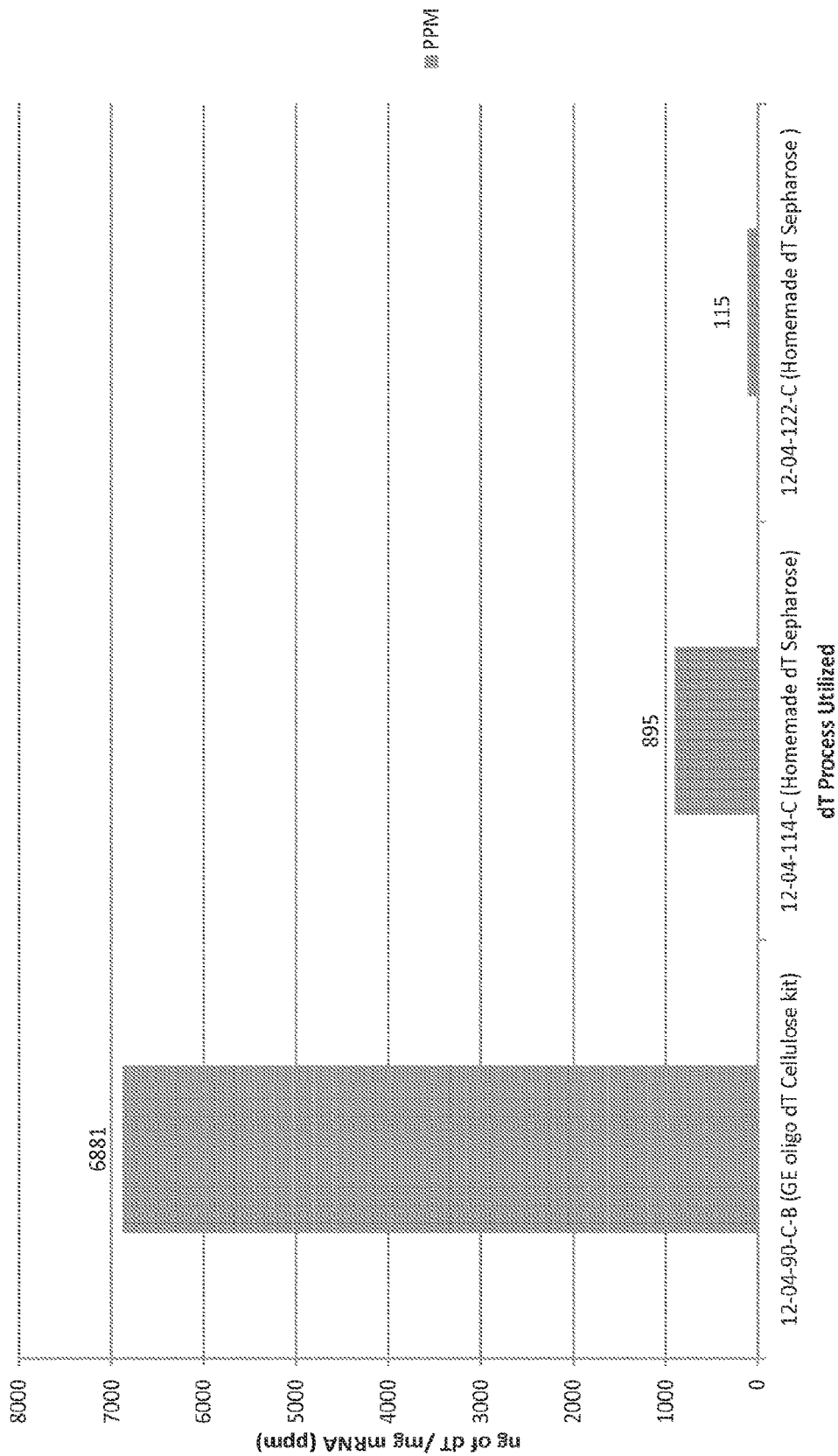
FIG. 5 shows poly dT column leaching analysis (LC-MS/MS based).

FIG. 5 denotes comparative leaching data of polythymidine ligand from mRNA lots purified using commercially available poly dT resin (GE cellulose) with mRNA lots purified using Applicant's dT resin. Lot 12-04-90-C-B represents GCSF encoded chemically modified mRNA purified using commercially available poly dT resin; this lot generated 6881 ppm leachate. Lot 12-04-114-C represents GCSF encoded chemically modified mRNA purified using Applicant's 20mer dT sepharose; this lot generated 895 ppm leachate Lot 12-04-122-C represents GCSF encoded chemically modified mRNA purified using Applicant's 20mer dT sepharose.; this lot generated 115 ppm leachate.

This demonstrates that dT ligand leaching generated per mg RNA from Applicant's dT resin was significantly less than commercially-available dT resin.

Example 3: Resin Re-Use Analysis

The resins (Sigma cellulose or Applicant's dT resin) were packed into SPE columns and the purifications were performed on a solid phase extraction vacuum manifold (Biotage). 1 gram of "Sigma dT Cellulose 1" (Sigma part #03131-1G) was packed in a 5 mL column. 150 mg of "Sigma dT Cellulose 2" (Part #75349-5G) was packed in a 5 mL column. 1 mL of 20mer Applicant's dT Sepharose was packed in a 5 mL column. Binding capacity experiments utilized GCSF PD 29 mRNA (encoding for GCSF and containing a 140A tail) as a feedstock and was loaded in excess onto each resin. The elutions were quantified by UV absorbance at 260 nm.

Figure 6:
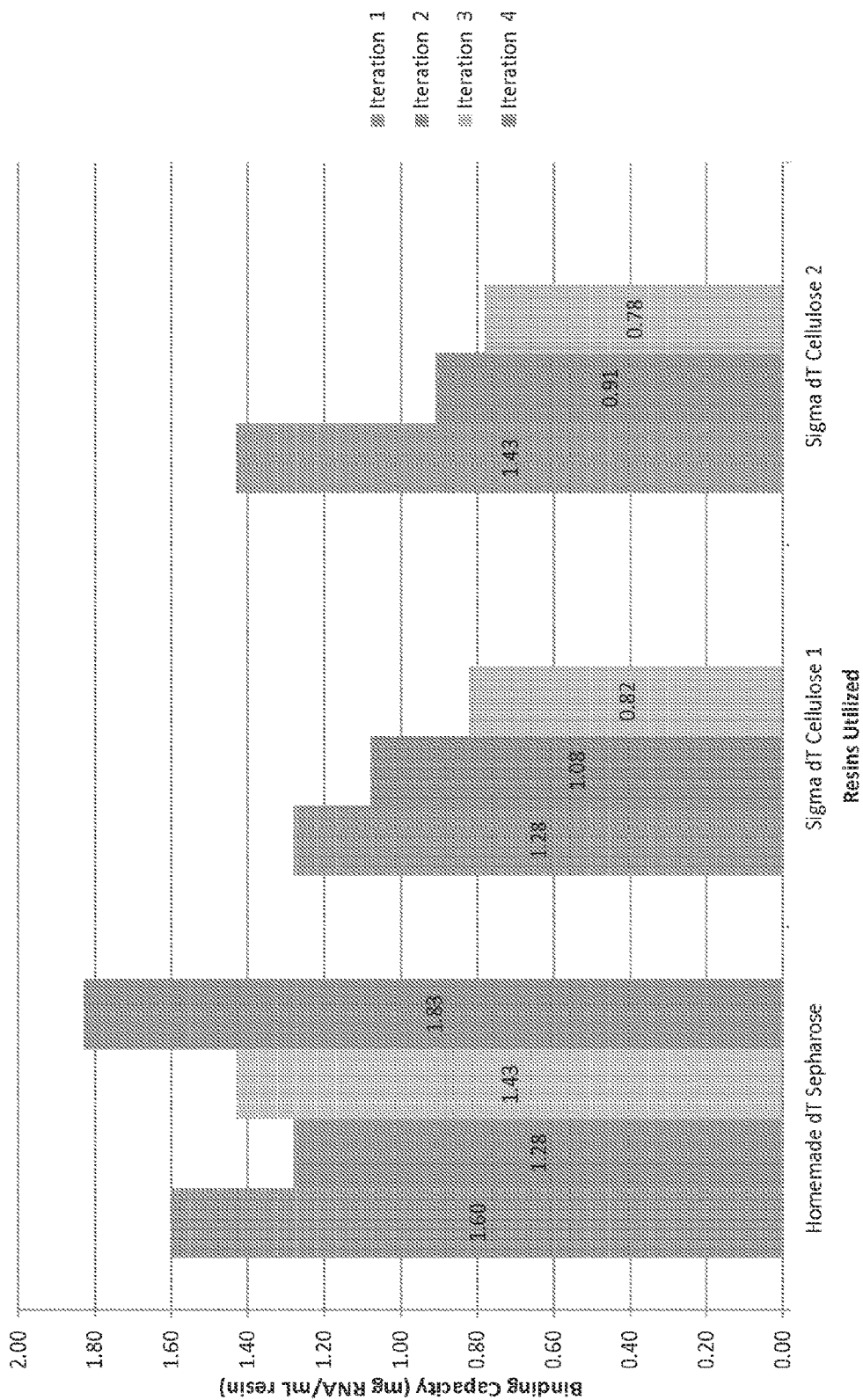
FIG. 6 shows a comparison of resin binding capacity between Applicant's poly dT resin and commercially-available dT resin upon reuse; (resin binding capacity vs. # of uses).

FIG. 6 shows a comparison of resin binding capacity between Applicant's poly dT resin and commercially available dT resin upon re-use (4 iterations/resin); (resin binding capacity vs. # of uses). Left to right in each experimental group: Iteration 1 is the first bar; iteration 2 is the second bar; iteration 3 is the third bar; and iteration 4 is the fourth bar (note that iteration 4 was not performed using the Sigma resin). The iterations were performed sequentially.

Diminishing binding capacity was seen as # of runs increase for Sigma's commercially available resin; in contrast Applicant's dT sephaorse resin does not exhibit a substantially reduced capacity.

Example 4: Endotoxin Analysis

Endotoxin Levels in mRNA batches following purification using various poly dT resins was analyzed. Endotoxin measurements were performed using a LAL-based assay Endosafe®-PTS™ instrument (Charles River Labs).

As seen in FIG. 7, a large abundance of endotoxin was present post dT purification using commercially available GE resin (samples 1-5). Applicant's dT resin actively clears endotoxin (samples 9-12).

Sample 5 (highly contaminated with endotoxin >46 EU/mg) was further purified using a column packed with Applicant's dT resin; After one round of purification (Sample 6) endotoxin was cleared significantly to 2.19 EU/mg; After a second round of purification with Applicant's oligo dT resin, endotoxin levels were reduced below the limit of quantitaion, <0.12 EU/mg (Sample 7).

From this data set it is apparent that eluted material using commercially available dT resin contains RNA highly contaminated with endotoxin. Applicant's dT resin was able to actively remove endotoxin from samples highly contaminated with endotoxin.

Example 5: DNA Removal Analysis

A 65 mg batch of chemically modified GCSF encoded mRNA, Lot 12-04-111-1 (922 bases), was transcribed with T7 RNA polymerase (12,740 units) using 1.46 mg of a 3781 base pair linearized plasmid template containing a T7 promoter and a 141 base poly A:T tract for 4 hours at 37° C. The transcription reaction was diafiltered into water using 100 kDa MWCO Amicon filters (EMD Millipore). The mRNA was subsequently purified on an AKTA Avant 150 (GE Healthcare) chromatography system using 100 mL of Applicant's 20mer dT Sepharose resin packed in a 5 cm id×5.1 cm glass column. The column was equilibrated using 0.5M NaCl 10 mM Tris HCl 1 mM EDTA pH 7.4. The RNA was preheated to 65° C. prior to loading using an inline mobile phase heater (Timberline Instruments), was loaded at 100 cm/h, in the aforementioned buffer. After loading, 2CV of high salt buffer was charged over the column, followed by 2CV of 0.1M NaCl 10 mM Tris HCl pH 7.4 to wash off weakly bound species. The polyadenylated RNA was eluted at 65° C. into 10 mM Tris HCl 1 mM EDTA pH 7.4. The flowthrough fraction and elution fraction were dia-filtered into water and concentrated using 100 kDa MWCO Amicon spin filters (EMD Millipore). The eluted material was quantified and the RNA quality was assessed via chip based electrophoresis using a Biorad Experion Bioanalyzer system.

Figure 8:
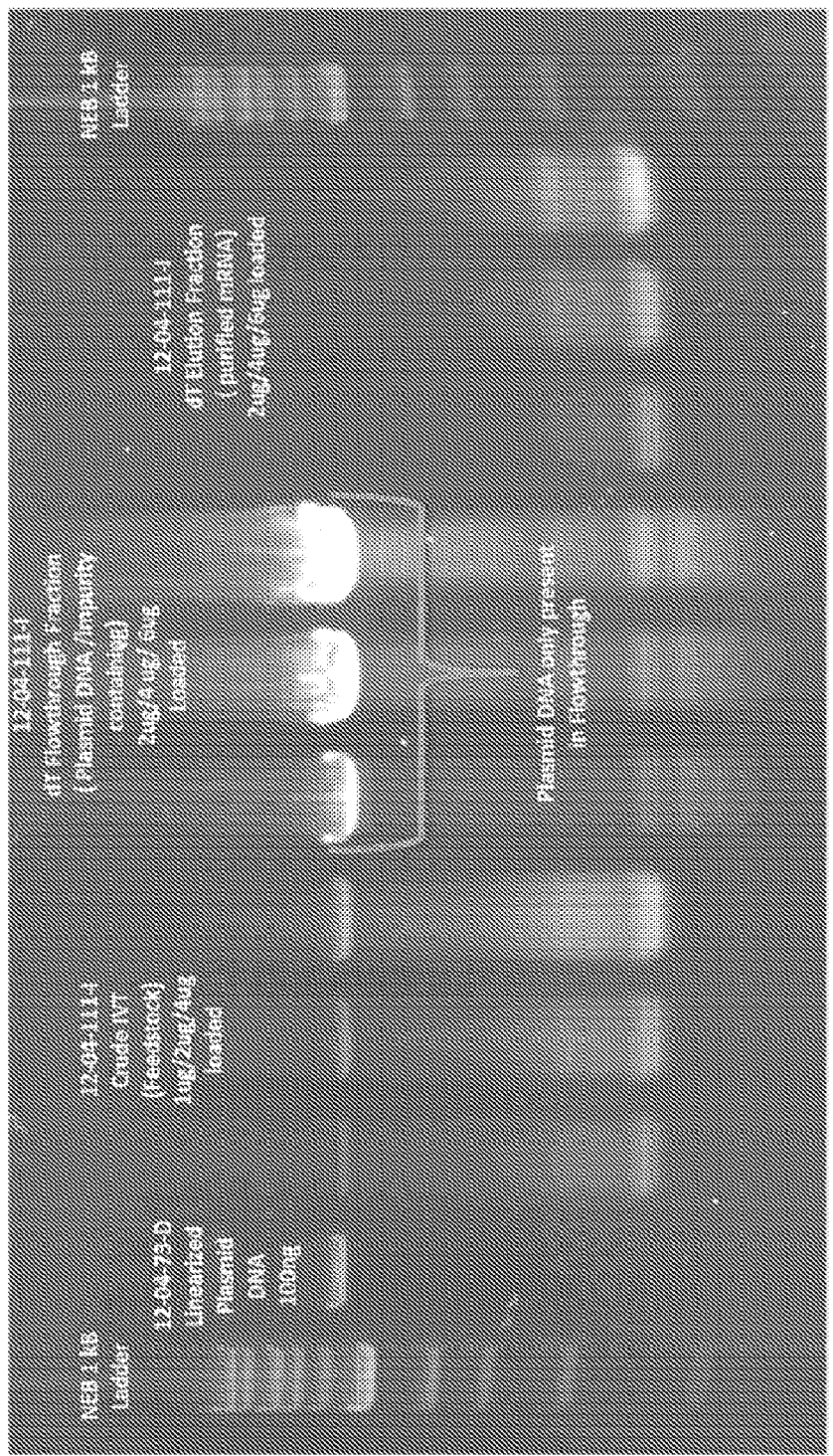
FIG. 8 shows a 1.2% Agarose gel used to assess plasmid DNA removal in lot 12-04-111-I.
Figure 9:
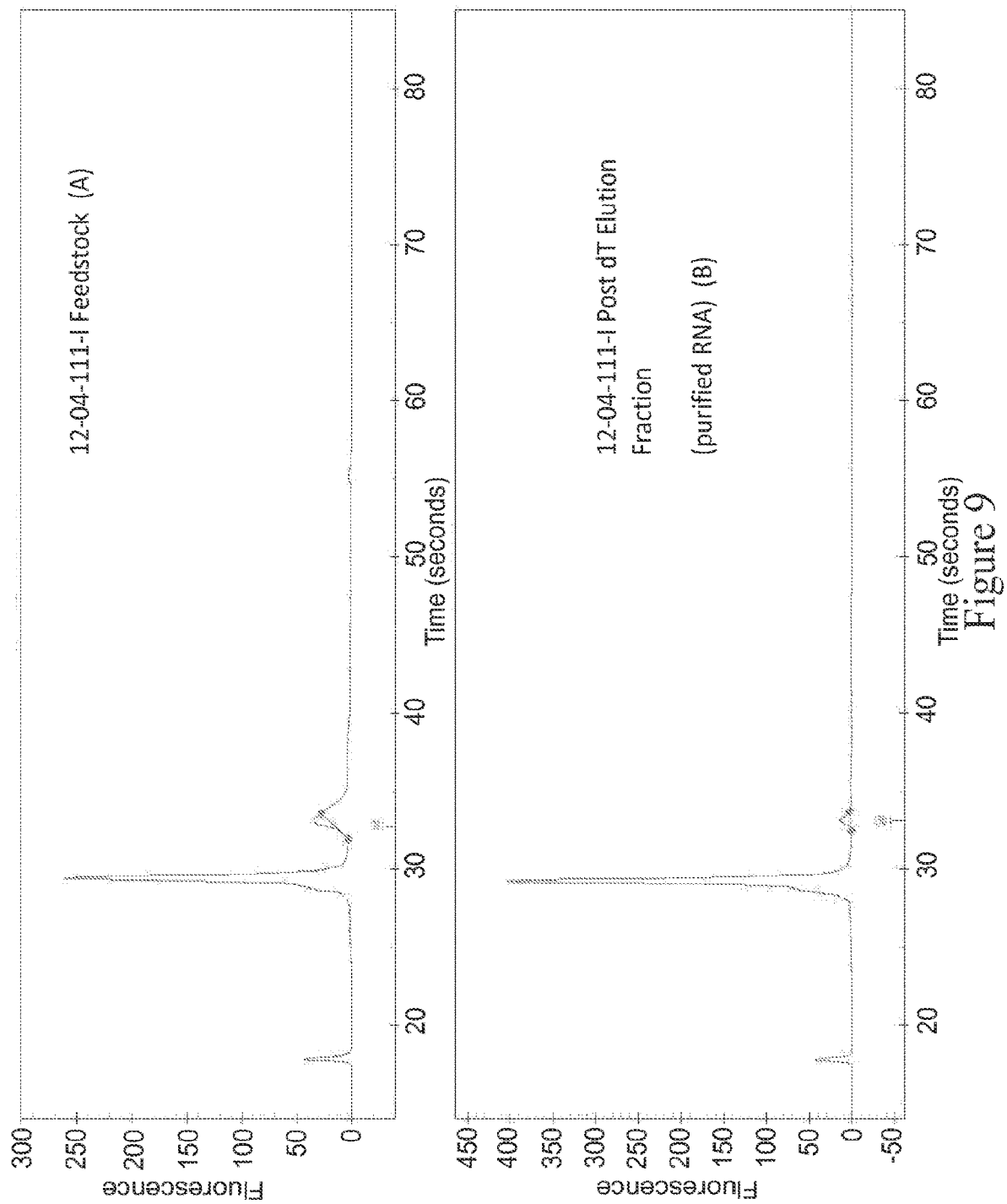
FIG. 9 shows Bioanalyzer electropherograms used to assess mRNA quality after dT sepharose purifications.
Figure 10:
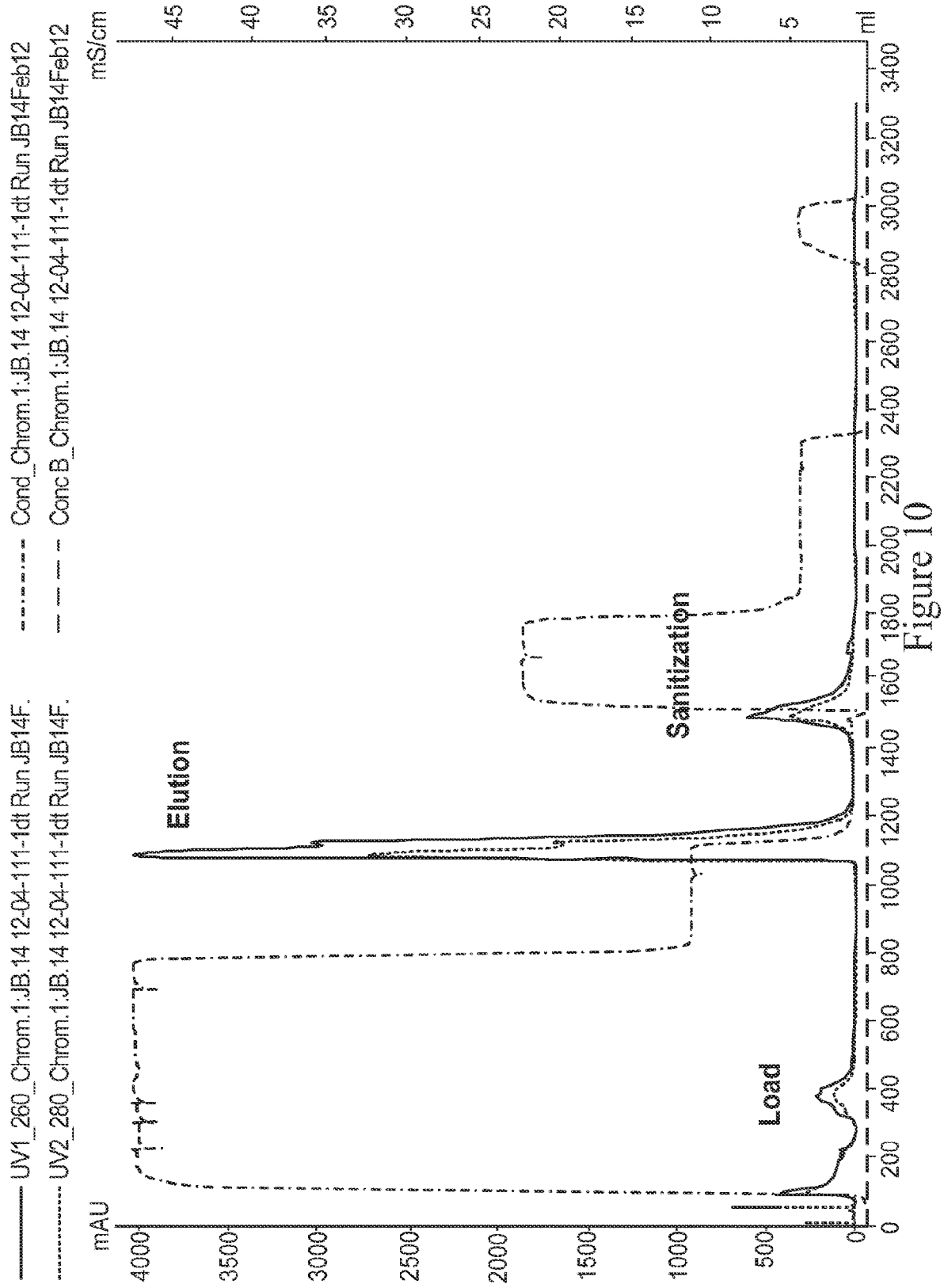
FIG. 10 shows a preparative UV Chromatogram from dT Sepharose Purification of 12-04-111-I.

By UV quantitation at 260 nm, 92% of total OD260 loaded was recovered. DNA removal was assessed using a 1.2% agarose precast SybrSafe gel (Life Technologies). As seen in FIG. 8, removal of plasmid DNA template was observed in the flowthrough fraction. The elution fraction containing purified mRNA shows no detectable plasmid DNA band. The published limit of detection on this gel is 0.5 ng/band. No DNA was detected upon loading 6 ug of RNA (elution), which denotes levels of DNA present in the RNA sample are less than 83 PPM. mRNA quality pre and post dT purification can be seen referring to the gel electropherogram in FIG. 9. The preparative UV chromatogram from the dT purification of 12-04-111-I can be seen in FIG. 10.

From this experiment, it is evident that Applicants 20 mer dT Sepharose resin facilitated the removal of plasmid DNA template from the RNA transcript.

Example 6: DNA Removal Analysis (2)

Figure 11:
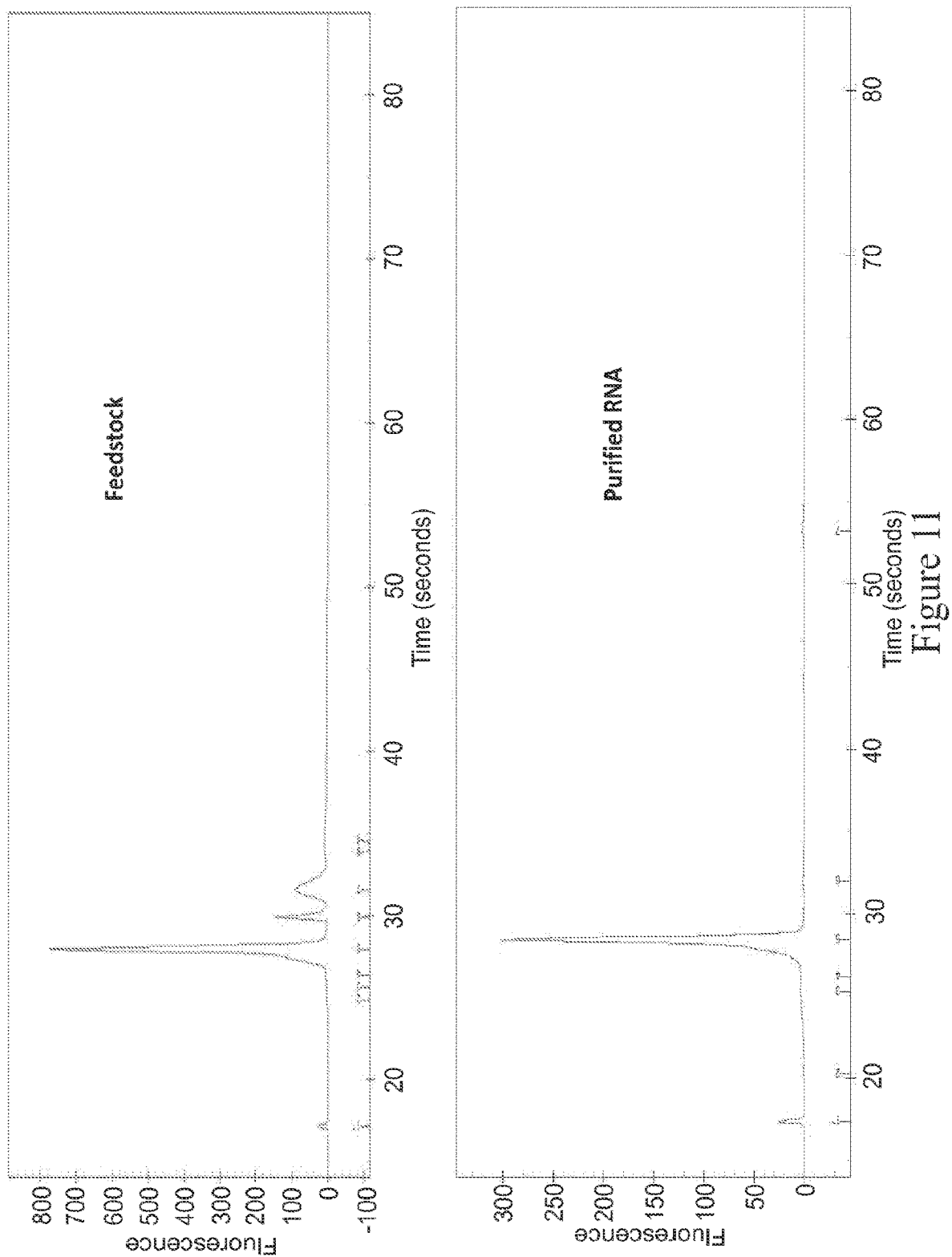
FIG. 11 shows an RNA Quality Assessment of 12-04-1014 by Bioanalyzer chip based electrophoresis.

A 5 mg batch of chemically modified GCSF encoded mRNA, Lot 12-04-101-1 (922 bases), was transcribed with T7 RNA polymerase (7,000 units) using 250 ug of a 3781 base pair linearized plasmid template containing a T7 promoter and a 141 base poly A:T tract for 4 hours at 37° C. This was a relatively high load of DNA in the transcription reaction. The transcription reaction was diafiltered into water using 100 kDa MWCO Amicon filters (EMD Millipore). 2 mg of mRNA was subsequently purified on a solid phase extraction vacuum manifold (Biotage) using 3 mL of Applicant's 20mer dT Sepharose resin packed in a 10 mL SPE column. The column was equilibrated using 0.5M NaCl 10 mM Tris HCl 1 mM EDTA pH 7.4. The RNA was preheated to 65° C. prior to loading using a water bath and was loaded in the aforementioned buffer. After loading, 2CV of high salt buffer was charged over the column, followed by 2CV of 0.1M NaCl 10 mM Tris HCl pH 7.4 to wash off weakly bound species. The polyadenylated RNA was eluted at 65° C. into 10 mM Tris HCl 1 mM EDTA pH 7.4 using pre-heated buffer. The flowthrough fraction and elution fraction were diafiltered into water and concentrated using 100 kDa MWCO Amicon spin filters (EMD Millipore). The eluted material was quantified and the RNA quality was assessed via chip based electrophoresis using a Biorad Experion Bioanalyzer system (FIG. 11).

Figure 12:
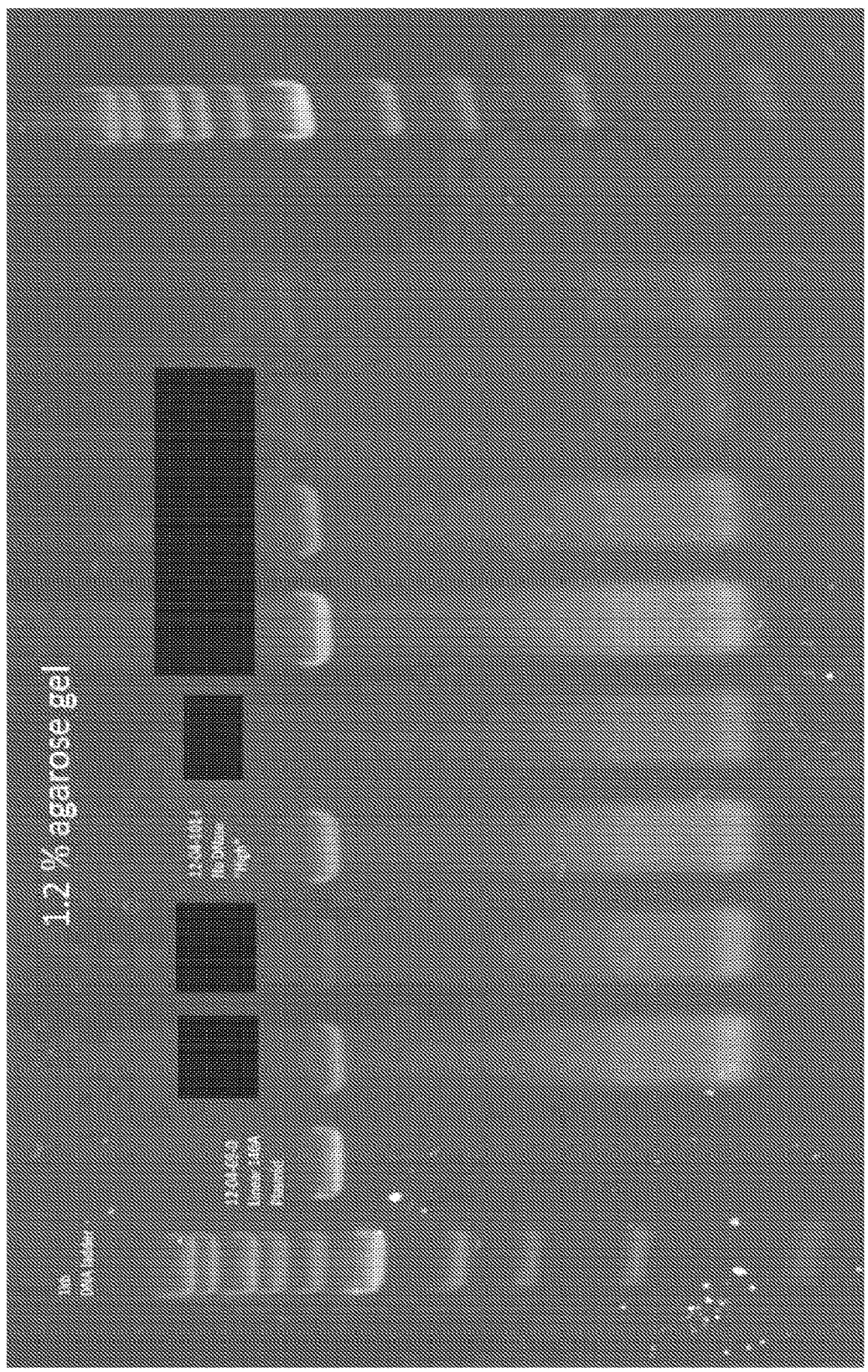
FIG. 12 shows a 1.2% agarose gel of 12-04-101-I Crude IVT Feedstock pre dT.
Figure 13:
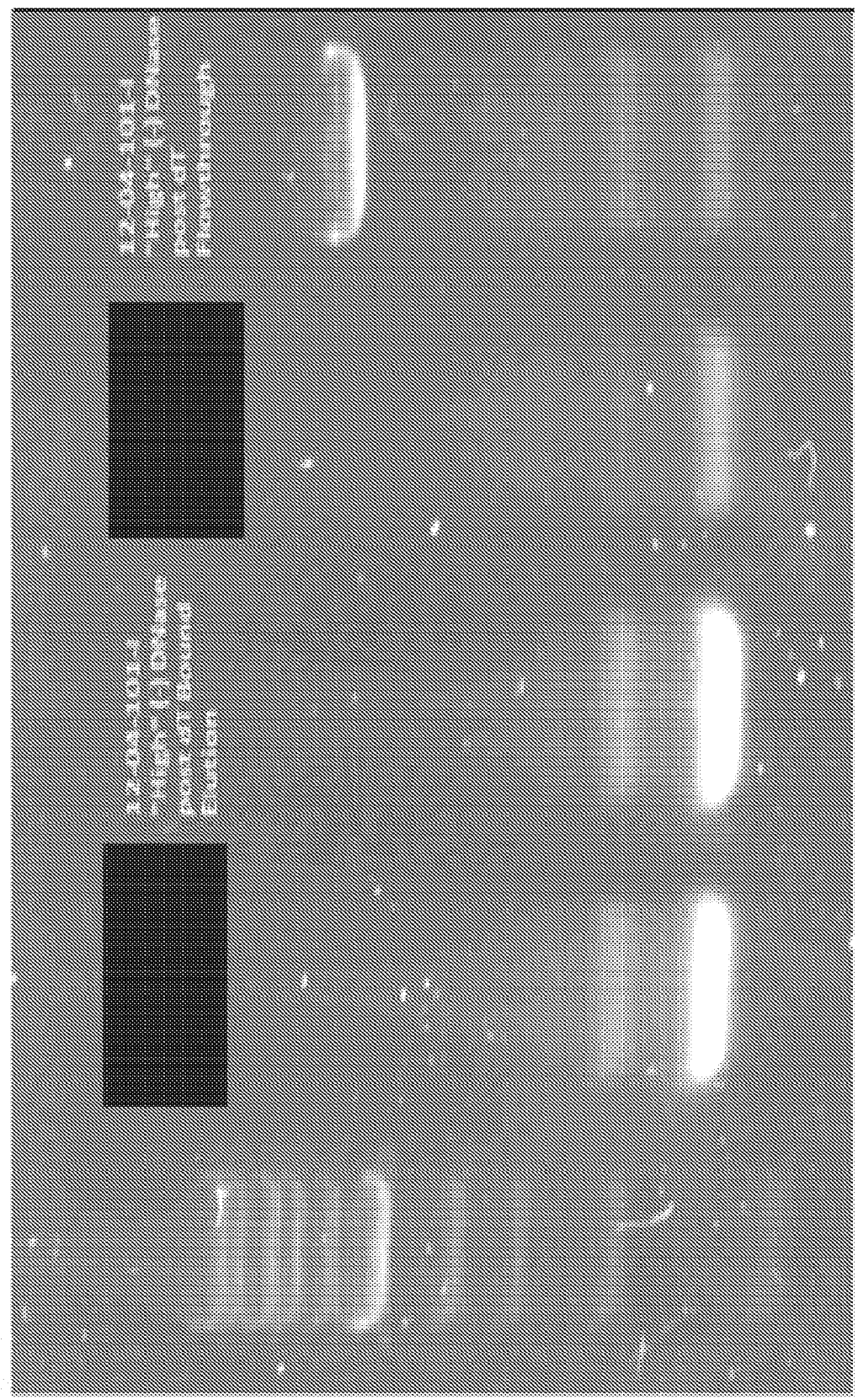
FIG. 13 shows a 1.2% agarose gel of 12-04-101-I Post dT Purification.

By UV quantitation at 260 nm, 91% of total OD260 loaded was recovered. DNA removal was assessed using a 1.2% agarose precast SybrSafe gel (Life Technologies). As seen in FIG. 12 and FIG. 13, removal of plasmid DNA template was observed in the flowthrough fraction. The elution fraction containing purified mRNA showed no detectable plasmid DNA band. The published limit of detection on this gel is 0.5 ng/band. No DNA was detected upon loading 1.5 ug of RNA (elution), which denotes levels of DNA present in the RNA sample are less than 333 PPM.

From this experiment, it is evident that Applicants 20 mer dT Sepharose resin facilitated the removal of plasmid DNA template from the RNA transcript.

Example 7: Resin Robustness Analysis

Lot 12-04-79-I mRNA post in vitro transcription was purified at large scale. The lot was broken into 4 purification runs. All four runs were performed sequentially. The RNA was purified using a 100 mL column (3.5 cm id×10.4 cm) packed with 20mer dT sepharose on a Biorad Duoflow FPLC system. The column was equilibrated using 0.5M NaCl 10 mM Tris HCl 1 mM EDTA pH 7.4. The RNA was preheated to 65° C. prior to loading using an inline mobile phase heater (Timberline Instruments), was loaded at 100 cm/h, in the aforementioned buffer. After loading, 2CV of high salt buffer was charged over the column, followed by 2CV of 0.1M NaCl 10 mM Tris HCl pH 7.4 to wash off weakly bound species. The polyadenylated RNA was eluted at 65° C. into 10 mM Tris HCl 1 mM EDTA pH 7.4. The eluted material was quantified and the RNA quality was assessed via chip-based electrophoresis using a Biorad Experion Bioanalyzer system.

Figure 15:
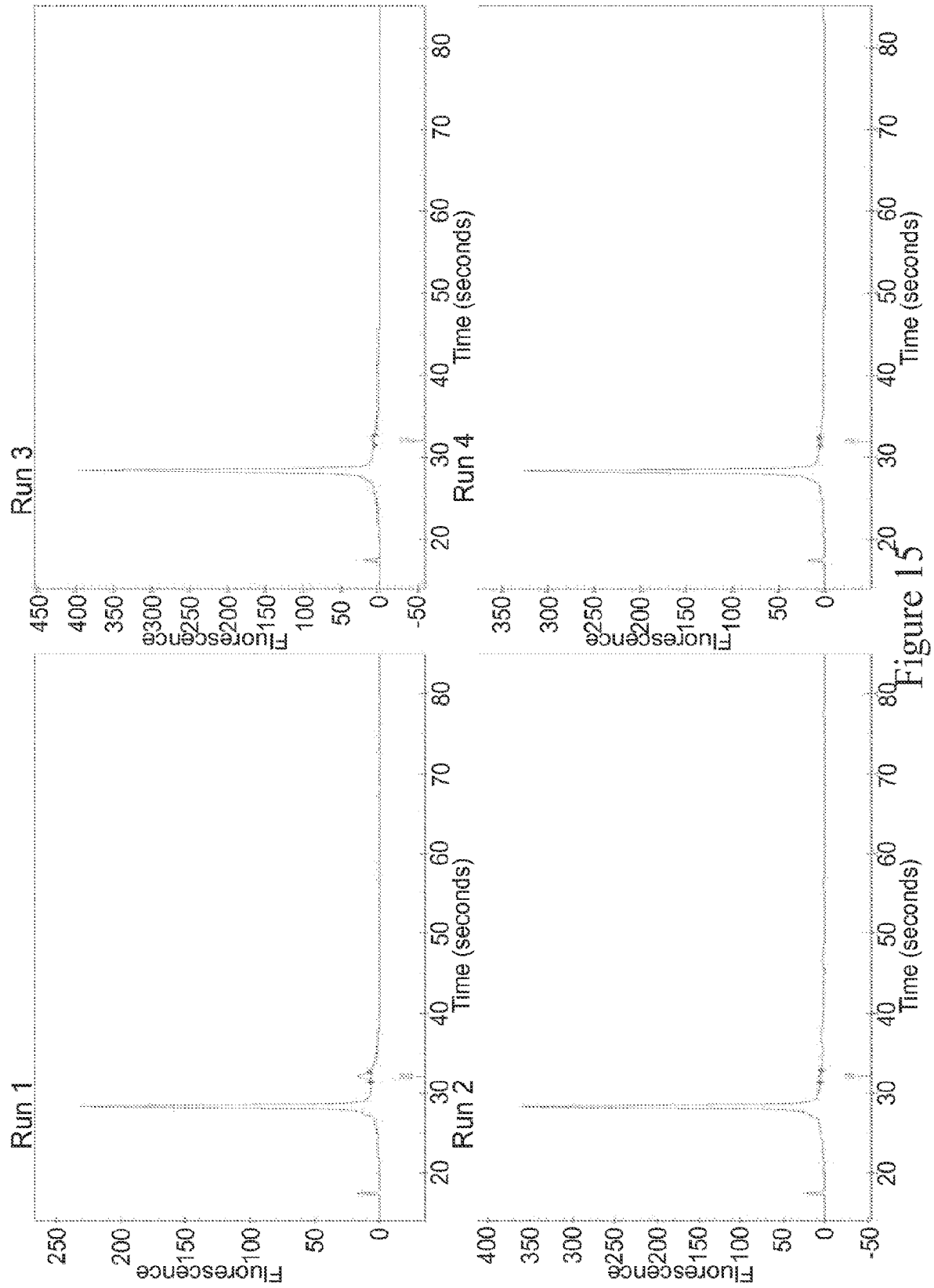
FIG. 15 shows mRNA quality assessment data of 4 consecutive large scale purifications of lot 12-04-79-I via Bioanalyzer chip-based electrophoresis.

By UV quantitation at 260 nm, yield can be seen in FIG. 14. RNA quality can be seen in the Bioanalyzer gel electropherograms of FIG. 15. Yield and purity were both consistent across four consecutive runs demonstrating resin robustness.

Example 8: 20-Mer Vs. 50-Mer Polythymidine Ligand Length Comparison Analysis

To compare polythymidine ligand lengths, 4 lots of resin were synthesized. Two were synthesized using a 20mer polythymidine (2' deoxy) oligonucleotide containing a 5' hexylamine linker and was conjugated to NHS activated Sepharose 4 FF resin. The other two were synthesized using a 50mer polythymidine (2' deoxy) oligonucleotide containing a 5' hexylamine linker and was conjugated to NHS activated Sepharose 4 FF resin. Two different ligand loadings were used for each ligand length, 7 mg ligand/mL resin and 15 mg ligand/mL resin. Both ligands were synthesized using solid phase synthetic methods, HPLC purified, and lyophilized. All dT sepharose resin preps (4) were synthesized in parallel using the same methodology at 5 mL scale (resin). To assess maximum binding capacity, the resins were saturated with the ligand. 35 mg of each ligand (for each 7 mg ligand/mL resin prep) was dissolved in in a 100 mM sodium bicarbonate solution (pH-8.5) at ~15 mg/mL. 75 mg of each ligand (for each 15 mg ligand/mL resin prep) was dissolved in in a 100 mM sodium bicarbonate solution (pH-8.5) at ~15 mg/mL. Dimethylsulfoxide (DMSO) was added to the ligand containing solution to achieve final concentration of 5 mg/mL in 67/33 (v/v %) DMSO/100 mM NaHCO$_3$.

Activated resin (5 mL) was centrifuged at 4000 rpm to remove the Isopropanol, re-slurried, washed twice, each time with 1 resin volume equivalent 1 mM HCl for 5 minutes, the resin was centrifuged and HCl was poured off.

Upon complete removal of HCl, all polythymidine oligo solution (5 mg/mL in 67/33 (v/v %) DMSO/100 mM NaHCO$_3$ was added to each respective resin prep and re-slurried; the coupling reactions were performed at 25° C. for 4 hours under constant shaking using an orbital shaker to maintain consistent slurry and to prevent resin settling.

The reactions were centrifuged at 4000 rpm and the coupling solution was poured off and quantified by UV absorbance at 260 nm to assess coupling efficiency. All four preparations, the two loads for the 20mer and the two loads for the 50mer resin conjugates were confirmed to be saturated. See FIG. 16.

To block any remaining unconjugated sites on the resins, the resins were treated with 5 mL of 100 mM Tris HCl pH 8; the mixture was re-slurried and was allowed to react at 25° C. for 4 hours under constant shaking using an orbital shaker to maintain consistent slurry and to prevent resin settling. The reaction was centrifuged at 4000 rpm and the solution was poured off.

The resin was re-slurried and washed with 5 mL of 100 mM sodium acetate solution pH 5 for 5 minutes. The mixture was centrifuged at 4000 rpm and the solution was poured off.

The resin was re-slurried and washed with 425 mL of 100 mM Tris HCl solution pH 8 for 5 minutes. The mixture was centrifuged at 4000 rpm and the solution was poured off.

A 20%/80% water/ethanol (v/v %) solution was added to the resin; The resin was re-slurried a final time and was stored at 4° C.

Binding capacities were determined for the four preps and can be seen in FIG. 16. An excess of poly A (140) containing RNA, GCSF PD 29 was loaded onto 2 mL of each resin; The resins were packed into 5 mL SPE columns and the purifications were performed in parallel on a solid phase extraction vacuum manifold (Biotage). Both 20mer and 50mer polythymidine Sepharose preps could bind poly A containing RNA. 20mer dT produced higher binding capacities.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for purifying a ribonucleic acid (RNA) transcript comprising a polyA tail, the method comprising:
    a) obtaining a first sample comprising the RNA transcript, wherein the first sample comprises at least 5% impurities, and wherein the percentage of RNA transcript and the percentage of impurities are the inverse of each other;
    b) contacting the first sample with a surface linked to twenty thymidines via a linker under conditions such that the RNA transcript binds to the surface;
    c) eluting the RNA transcript from the surface; and
    d) collecting the RNA transcript in a second sample, wherein the level of impurities is lower in the second sample than the level of impurities in the first sample.

2. The method of claim 1, further comprising washing the surface with a solution after step b).

3. The method of claim 1, further comprising preheating the first sample before step b).

4. The method of claim 1, wherein one or more steps are performed using a batch process.

5. The method of claim 1, wherein the sample comprises deoxyribonucleic acid (DNA) and the sample has not been subjected to DNase treatment.

6. The method of claim 1, wherein the one or more impurities comprise an RNA that does not comprise a polyA tail, DNA, a carbohydrate, a toxin, a polypeptide, and/or a nucleotide.

7. The method of claim 1, wherein the contacting step is performed at a temperature of 65° C.

8. The method of claim 1, wherein the contacting step is performed at a rate of 100 cm/h.

9. The method of claim 1, wherein the RNA transcript and the twenty thymidines bind one another via non-covalent bonding.

10. The method of claim 1, wherein the first sample comprising the RNA transcript is a salt solution.

11. The method of claim 1, wherein the first sample comprising the RNA transcript is a sodium chloride solution.

12. The method of claim 1, wherein the elution step is performed with an elution buffer.

13. The method of claim 1, wherein the elution step is performed at a temperature of 65° C.

14. The method of claim 1, wherein the RNA transcript is the product of in vitro transcription using a non-amplified DNA template.

15. The method of claim 1, wherein the RNA transcript is 100 to 10,000 nucleotides in length.

16. The method of claim 1, wherein the method is repeated at least 2-times with the same surface.

* * * * *